(12) United States Patent
Converso et al.

(10) Patent No.: US 8,629,275 B2
(45) Date of Patent: Jan. 14, 2014

(54) AHCY HYDROLASE INHIBITORS FOR TREATMENT OF HYPER HOMOCYSTEINEMIA

(75) Inventors: Antonella Converso, Elkins Park, PA (US); Timothy J. Hartingh, Blue Bell, PA (US); Mark E. Fraley, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 303 days.

(21) Appl. No.: 13/060,775

(22) PCT Filed: Aug. 31, 2009

(86) PCT No.: PCT/US2009/055501
§ 371 (c)(1),
(2), (4) Date: Feb. 25, 2011

(87) PCT Pub. No.: WO2010/027935
PCT Pub. Date: Mar. 11, 2010

(65) Prior Publication Data
US 2011/0160229 A1    Jun. 30, 2011

Related U.S. Application Data

(60) Provisional application No. 61/191,328, filed on Sep. 8, 2008.

(51) Int. Cl.
C07D 471/02    (2006.01)

(52) U.S. Cl.
USPC ........................................................ 546/113

(58) Field of Classification Search
USPC ............................................. 546/263.4, 113
See application file for complete search history.

(56) References Cited

U.S. PATENT DOCUMENTS

| | | | |
|---|---|---|---|
| 4,859,677 A | 8/1989 | Borchardt et al. | |
| 4,968,690 A | 11/1990 | Marquez et al. | |
| 5,039,689 A | 8/1991 | Daluge | |
| 5,688,774 A | 11/1997 | Jacobson et al. | |
| 6,262,241 B1 | 7/2001 | Cook et al. | |
| 6,284,748 B1 | 9/2001 | Dang et al. | |
| 6,593,306 B1 | 7/2003 | Chen et al. | |
| 2002/0058635 A1 | 5/2002 | Averett | |
| 2004/0138169 A1 | 7/2004 | Wieland | |

FOREIGN PATENT DOCUMENTS

| | | |
|---|---|---|
| CN | 1626088 * | 6/2005 |
| EP | 0 431 799 A2 | 6/1991 |
| EP | 0 510 260 A2 | 10/1992 |
| WO | 90/09177 A1 | 8/1990 |
| WO | 91/10671 A1 | 7/1991 |
| WO | 98/16184 A2 | 4/1998 |
| WO | 01/19360 A2 | 3/2001 |
| WO | 02/074910 A2 | 9/2002 |
| WO | 02/074910 A3 | 9/2002 |
| WO | 03/061576 A2 | 7/2003 |
| WO | 03/061576 A3 | 7/2003 |
| WO | 2004/002999 A2 | 1/2004 |
| WO | 2004/002999 A3 | 1/2004 |
| WO | 2007047793 A2 | 4/2007 |
| WO | 2007/100304 A1 | 9/2007 |
| WO | 2010/036213 A1 | 4/2010 |

OTHER PUBLICATIONS

Gonzlez-Diaz et al Bio Med Chem Lett 2005, 13, 601-608—abstract.*
Gonzlez-Diaz et al Bio Med Chem Lett 2005, 15, 1651-1657—abstract.*
Montgomery et al Biol Methylation Drug Des 1986, 409-16—abstract.*
Montgomery et al Journal of Medicinal Chemistry 1982, 25, 626-9.*
Ando, T., et al., "Synthesis of 2-modified aristeromycins and their analogs as potent inhibitors agains Plasmodium falciparum S-adenosyl-L-homocysteine hydrolase", Bioorganic & Medicinal Chemistry, vol. 16 (2008) 3809-3815.
Wolfe, M. S., et al., "4'-Modified Analogues of Aristeromycin and Neplanocin A: Synthesis and Inhibitory Activity toward S-Adenosyl-L-homocysteine Hydrolase", J. Med. Chem., vol. 35 (1992) 1782-1791.
Borchardt, R. T., et al., "S-Aristeromycinyl-L-homocysteine, a Potent Inhibitor of S-Adenosylmethionine-Dependent Transmethylations", J. of Med. Chem., vol. 19, No. 1 (1976) 197-198.
Borcherding, D. R., et al., "Synthesis of Analogues of Neplanocin A: Utilization of Optically Active Dihydroxycyclopentenones Derived from Carbohydrates", J. Org. Chem., vol. 52, No. 24 (1987) 5457-5461.
Cheikh, A. B., et al., "Synthesis of Racemic 6' beta-Hydroxyaristeromycin. A Hydroxycarbocyclic Analogue of Adenosine", The Journal of Organic Chemistry, vol. 53, No. 5 (1988) 929-936.

(Continued)

*Primary Examiner* — John Mabry
(74) *Attorney, Agent, or Firm* — Kenrick L. Vidale; Anna L. Cocuzzo; John C. Todaro

(57) ABSTRACT

The present invention is directed to AHCY inhibitors of formula (I): which are useful in the treatment of diseases characterized by high homocysteine levels, such as Alzheimer's disease. The invention is also directed to pharmaceutical compositions comprising the compounds, and to the use of the compounds and compositions in the treatment of diseases characterized by high homocysteine levels.

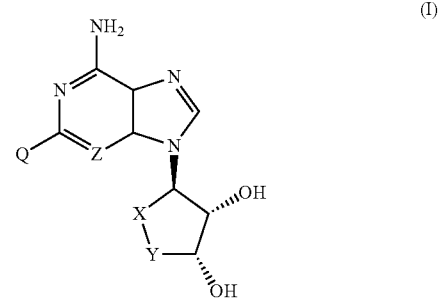

(I)

16 Claims, No Drawings

(56) References Cited

OTHER PUBLICATIONS de Zwart, M., et al., "A Functional Screening of Adenosine Analogues at athe Adenosine A2B Receptor: A Search for Potent Agonists", Nucleosides & Nucleotides, vol. 17, No. 6 (1998) 969-985.

Fukukawa, K., et al., "Synthesis of 2'(r)-Substituted Neplanocin A's (Nucleosides and Nucleotides. XXXII", Chem. Pharm. Bull. vol. 29, No. 2 (1981) 597-600.

Gao, Z. G., et al., "Structural determinants of efficacy at A3 adenosine receptors: modification of the ribose moiety", Biochemical Pharmacology, vol. 67, No. 5 (2004) 893-901.

Hong, J. H., et al., "An Efficient Synthesis of Carbocyclic Nucleosides with Use of Ring-Closing Metathesis from D-Lactose", J. Org. Chem., vol. 67, No. 19 (2002) 6837-6840.

Jeong, L. S., et al., "Synthesis of Halogenated 9-(Dihydroxycyclpen-4'-enyl) Adenines and Their inhibitory Activities Against S-Adenosylhomecysteine Hydrolase", Nucleosides, Nucleotides & Nulceic Acids, vol. 22, Nos. 5-8 (2003) 919-921.

Matuszewska, B. A., et al., "The Mechanism of Inhibition of Alcaligenes faecalis S-Adenosylhomocysteine Hydrolase by Neplanocin A1", Archives of Biochemistry and Biophysics, vol. 256, No. 1 (1987) 50-55.

Kapeller, H., et al., "Synthetic Studies towards (±)-Aristeromycin and its 5'-homo-Analogue", Monashefte für Chemie, vol. 128 (1997) 191-200.

Katagiri, N., et al., "Explanation for Stereoselectivity of the CIS-Dihydroxylation of CIS-3,5-Disubstituted Cyclopentenes", Chem. Pharm. Bull., vol. 42, No. 12 (1994) 2653-2655.

Kim, H. O., et al., "Synthesis of fluorinated cyclopentenyladenine as potent inhibitor of S-adenosylhomocysteine hydrolase", Bioorganic & Medicinal Chemistry Letters, vol. 14 (2004) 2091-2093.

Kitade, Y., et al., "Synthesis of 2-Fluoronoraristeromycin and its Inhibitory Activity against Plasmodium falciparum S-Adenosyl-L-homocysteine Hydrolase", Bioorganic & Medicinal Chemistry Letters, vol. 13, No. 22 (2003) 3963-3965.

Kitade, Y., et al., "4.-Fluorinated carbocyclic nucleosides: Synthesis and inhibitory activity against S-adenosyl-L-homocysteine hydrolase", Bioorganic & Medicinal Chemistry, vol. 14, No. 16 (2006) 5578-5583.

Kitade, Y., et al., "Synthesis of base-modified noraristeromycin derivatives and their inhibitory activity against human and Plasmodium Falciparum recombinant S-adenosyl-L-homocysteine hydrolase", Tetrahedron, vol. 58, No. 7 (2002) 1271-1277.

Kojima, H., et al., "Synthesis of 3', 4'-epoxynoraristeromycin analogs for molecular labeling probe of S-adenosyl-L homocysteine hydrolase", Bioorganic & Medicinal Chemistry, vol. 16, No. 13 (2008) 6575-6579.

Kumamoto, H., et al., "Synthesis of Novel 4'-Modified Neplanocin A Analogues and their Inhibitory Activity Against S-Adenosyl-L-I-homocysteine Hydrolase", Nucleosides, Nucleotides, and Nucleic Acids, vol. 26 (2007) 733-736.

Madhavan, G. V. B., et al., "Synthesis and Antiviral Evaluation of 6'-Substituted Aristeromycins: Potential Mechanism-Based Inhibitors of S-Adenosylhomocycsteine Hydrolase", J. Med. Chem., vol. 31, No. 9 (1988) 1798-1804.

Matthews, D. P., et al., "(E) and (Z) 5'-Fluoro Olefin Carbocyclic Nucleosides: Effect of Olefin Geometry on Inhibition of S-Adenosyl-L-Homocysteine Hydrolase", Bioorganic & Medicinal Chemistry Letters, vol. 13, No. 2 (1993) 165-168.

Moon, H. R., et al., "Synthesis of 5'-substituted fluoro-neplanocin A analogues: importance of a hydrogen bonding donor at 5'-position for the inhibitory activity of S-adenosylhomocysteine hydrolase", Bioorganic & Medicinal Chemistry Letters, Vo. 14, No. 22 (2004) 5641-5644.

Obara, T., et al., "New Niplanocin Analogues. 7. Synthesis and Antiviral Activity of 2-Halo Derivatives of Neplanocin A", J. Med. Chem., vol. 39, No. 19 (1996) 3847-3852.

Prytz, P. S., et al., "Elevation of Cyclic AMP Levels in HL-60 Cells Accumulated in G1 or G2 by Transmethylation Inhibitors", Biochemical Pharmacology, vol. 42, No. 9 (1991) 1761-1766.

Roy, A., et al., "The 4', 4'-difluoro analog of 5'-noraristeromycin: A new structural prototype for possible antiviral drug development toward orthopoxvirus and cytomegalovirus", Bioorganic & Medicinal Chemistry, vol. 13 (2005) 4443-4449.

Roy, A., et al., "Enantiospecific synthesis of 5',5',5'-trifluoro-5'-deoxyneplanocin A", Tetrahedron Letters, vol. 46, No. 51 (2005) 8913-8915.

Saso, Y., et al., "S-Adenosyl-L-homocysteine Hydrolase Inhibitor Mediates Immunosuppressive Effects in Vivo: Suppression of Delayed Type Hypersensitivity Ear Swelling and Peptidoglycan Polysaccharide-Induced Arthritis", The Journal of Pharmacology and Experimental Therapeutics, vol. 296, No. 1 (2001) 106-112.

Ye, W., et al., "5'-Methylaristeromycin and Related Derivatives", J. Org. Chem., vol. 71, No. 22 (2006) 8641-8643.

Shuto, S., et al., "New Neplanocin Analogues. IV. 2-Fluoroneplanocin A: An Adenoseine Deaminase-Resistant Equivalent of Neplanocin A", Chem. Pharm. Bull., vol. 42, No. 8 (1994) 1688-1690.

Shuto, S., et al., "New Neplanocin Analogues. VIII. Synthesis and Biological Activity of 6'-C-Ethyl, -Ethenyl, and -Ethynyl Derivatives of Neplanocin A", Chem. Bull. Pharm., vol. 45, No. 7 (1997) 1163-1168.

Shuto, S.,. et al., "New Neplanocin Analogues. 1. Synthesis of 6'-Modified Neplanocin A derivatives as Broad Spectrum Antiviral Agents", J. Med. Chem., vol. 35, No. 2 (1992) 324-331.

Shuto, S., et al.,"New Neplanocin Analogues. 6. Synthesis and Potent Antiviral Activity of 6'-Homoneplanocin A", J. Med. Chem., vol. 39, No. 12 (1996) 2392-2399.

Shuto, S., et al., "New Neplanocin Analogues. 12. Alternative Synthesis and Antimalarial effect of (6'R)-6'-C Methylneplanocin A, a Potent AdoHcy Hydrolase Inhibitor", J. Med. Chem., vol. 45, No. 1 (2002) 748-751.

Siddiqi, S. M., et al., "Enantiospecific Synthesis of the Fluoro and Epimeric Derivatives of 5'-Noraristeromycin", J. Chem. Soc., Chem. Commun., No. 8 (1993) 708-709.

Siddiqi, S. M., et al., "Search for New Purine- and Ribose-Modified Adenosine Analogues as Selective Agonists and Antagonists at Adenosine Receptors", vol. 38, No. 7 (1995) 1174-1188.

Tanaka, N., et al., "Crystal Structure of S-Adenosyl-L-Homocysteine Hydrolase from the Human Malaria Parasite Plasmodium falciparum", J. Mol. Biol., vol. 343, No. 4 (2004) 1007-1017.

Trost, B. M., et al., "A Transition-Metal-Controlled Synthesis of (±)-Aristeromycin and (±)-2',3'-diepi-Aristeromycin. An unusual Directive Effect in Hydroxylations", J. Am. Chem. Soc., vol. 110 (1988) 621-622.

Tseng, C. K. H., et al., "Synthesis of 3-Deazaneplanocin A, a Powerful Inhibitor of S-Adenosylonocysteine Hydrolase with Potent and Selective in Vitro and in Vivo Antiviral Activities", J. Med. Chem., vol. 32, No. 7 (1989) 1442-1446.

Tseng, C. K. H., et al., "An Improved Method of Synthesis of Neplanocin and Related Cyclopentenyl-Containing Nucleosides", Tetrahedron Letters, vol. 26, No. 31 (1985) 3669-3672.

Wang, M., et al., "Effects of Ligand Binding and Oxidation on Hinge-Bending Motions in S-Adenosyl-L-homocysteine Hydrolase", Biochemistry, vol. 45, No. 25 (2006) 7778-7786.

Yin, X., et al., "Chiral syntheses of 6'-β-fluoroaristeromycin, 6'-β-fluoro-5'-nonaristeromycin and aristeromycin", vol. 46., No. 44 (2005) 7535-7538.

Zulfiqar, F., et al., "Synthesis of Carbocyclic 2-Substituted Adenine Nucleoside and Related Analogs", Nucleosides, Nucleotides and Nucleic Acids, vol. 27, Nos. 10-11 (2008) 1153-1157.

Shealy, Y. F., et al., "9-[β-DL-2α,3α-Dihydroxy-4β-(hydroxymethyl)-cyclopentyl]adenine, the Carbocyclic Analog of Adenosine", J. Am. Chem. Soc., vol. 88, No. 16 (1966) 3885-3887.

DeClercq, E., "Carbocyclic Adenosine Analogues As S-Adenosylhomocysteine Hydrolase inhibitors and Antiviral Agents: Recent Advances", Nucleosides, Nucleotides and Nucleic Acids, vol. 17, Nos. 1-3 (1998) 625-634.

Daelemans, D., et al., "Stereospecificity of 6'-C-neplanocin A Analogues AS Inhibitors of S-Adenosylhomocysteine Hydrolase Activ-

(56) References Cited

OTHER PUBLICATIONS ity and Human Immunodeficiency Virus Replication", Nucleosides & Nucleotides, vol. 17, Nos. 1-3 (1998) 479-486.

Jones, M. F., et al., "Synthesis of Carbocyclic Nucleosides: Preparation of (−)-5'-Homoaristeromycin and Analogues", J. Chem. Soc. Perkin Trans., No. 11 (1998) 2927-2932.

Jeong, L. S., et al., "Design, Synthesis, and Biological Evaluation of Fluoroneplanocin A as the Novel Mechanism-Based Inhibitor of S-Adenosylhomocysteine Hydrolase", J. Med. Chem., vol. 46, No. 2 (2002) 201-203.

Ando, T., et al., "Synthesis of 4'-modified noraristeromycins to clarify the effect of the 4'-hydroxyl groups for inhibitory activity against S-adenosyl-L-homocysteine hydrolase", vol. 18, No. 8 (2008) 2615-2618.

Moon, H. R., et al., "Structure-Activity Relationship of 5'-Substituted Fluoro-Neplanocin A Analogues As Potent Inhibitors of S-Adenosylhomocysteine Hydrolase", vol. 24, Nos. 5-7 (2006) 707-708.

Roy, A., et al., "4'- and 1'-Methyl-Substituted 5'-Norcarbanucleosides", vol. 68, No. 24 (2003) 9269-9273.

Secrist III, J. A., et al., "Syntheses of 5'-Substituted Analogues of Carbocyclic 3-Deazaadenosine as Potential Antivirals", vol. 36, No. 15 (1993) 2102-2106.

Akdag, A et al., J. Phys. Chem., vol. 106, (2002), pp. 11254-11261, "Theoretical study of 9-beta-D-Erythrofuranosyladenine and corresponding carbocyclic analogues. Evidence for a base-activated conformational lock".

Ault-Riche, DB et al., Molecular Pharmacology, An International Journal, vol. 43, No. 6 (1993), pp. 989-997, "Effects of 4'-modified analogs of aristeromycin on the metabolism of s-adenosyl-L-homocysteine in murine L929 cells".

Barnard, DL et al., Antiviral Chemistry & Chemotherapy, vol. 12, No. 4, (2001), pp. 241-250, "Inhibition of measles virus replication by 5'-nor carbocyclic adenosine analogues".

Daelemans, D et al., Journal of Virological Methods, vol. 96, (2001), pp. 183-188, "A quantitative GFP-based bioassay for the detection of HIV-1 Tat transactivation inhibitors".

Daelemans, D et al., Molecular Pharmacology, vol. 52, (1997), pp. 1157-1163, "S-adenosylhomocysteine hydrolase inhibitors interfere with the replication of human immunodeficiency virus Type-1 through inhibition of the LTR transactivation".

Hasobe, M et al., Antiviral Chemistry & Chemotherapy, vol. 4, No. 4, (1993), pp. 245-248, "(1'R,2'S,3'R)-9-(2',3'-dihydroxycyclopentan-1-yl)ade-nine and -3-deaza-adenine: analogues of aristeromycin which exhibit potent antiviral activity with reduced cytotoxicity".

Henderson, DM et al., Molecular and Biochemical Parasitology, vol. 53, (1992), pp. 169-184, "Cloning of the gene encoding *Leishmania donovani* S-adenosylhomocysteine hydrolase, a potential target for antiparasitic chemotherapy".

Paisley, SD et al., Nucleosides & Nucleotides, vol. 8, (1989), pp. 689-698, "Elucidation of the mechanism by which 9-(trans-2',Trans-3'-dihydroxycyclopent-4'-enyl)-adenine inactivates S-adenosylhomocysteine hydrolase and elevates cellular levels of S-adenosylhomocysteine".

Snoeck, R et al., Antiviral Research, vol. 21 (1993), pp. 197-216, "Inhibitory activity of S-adenosylhomocysteine hydrolase inhibitors against human cytomegalovirus replication".

Turner, MA et al., Nature Structural Biology, vol. 5, No. 5, (1998), pp. 369-376, "Structure determination of selenomethionyl S-adenosylhomocysteine hydrolase using data at a single wavelength".

Villalon, MDG, et al., Antiviral Research, vol. 20, (1993), pp. 131-144, "Activity of several S-adenosylhomocysteine hydrolase inhibitors against African swine fever virus replication in Vero cells".

Yang, X et al., Archives of Biochemistry and Biophysics, vol. 383, No. 2, (2000), pp. 272-280, "Overexpression, purification, and characterization of S-adenosylhomocysteine hydrolase from *Leishmania donovani*".

Yeh, JC et al., Journal of Computer-Aided Molecular Design, vol. 5, (1991), pp. 213-234, "A molecular model for the active site of S-adenosyl-L-homocysteine hydrolase".

Yuan, CS et al., Biochemistry, vol. 32, (1993), pp. 10414-10422, "Ligand-dependent changes in intrinsic fluorescence of S-adenosylhomocysteine hydrolase: Implications for the mechanism of inhibitor-induced inhibition".

Gassner, ND et al., J. Natl. Prod., vol. 70, (2007), pp. 383-390, "Accelerating the Discovery of Biologically Active Small Molecules Using a High-Throughput Yeast Halo Assay".

Pankaskie, MC et al., J. Med. Chem., vol. 28 (1985), pp. 1117-1119, "Inhibition of Muscarinic Receptor Binding and Acetylcholine-Induced Contraction of Guinea Pig Ileum by Analogues of 5'-(Isobutylthio)adenosine".

Yang, M et al., Tetrahedron Letters, vol. 45 (2004), pp. 8981-8982, "An efficient synthesis of (-)-3-deazaaristeromycin".

Yang, M et al., Tetrahedron Letters, vol. 62 (2006), pp. 1295-1300, "The Mitsunobu reaction in preparing 3-deazapurine carbocyclic nucleosides".

\* cited by examiner

AHCY HYDROLASE INHIBITORS FOR TREATMENT OF HYPER HOMOCYSTEINEMIA

CROSS-REFERENCE TO RELATED APPLICATIONS

This application is a U.S. National Phase application under 35 U.S.C. §371 of PCT Application No. PCT/US2009/055501, filed Aug. 31, 2009, which claims priority from and the benefit of U.S. Provisional Application No. 61/191,328, filed Sep. 8, 2008.

FIELD OF THE INVENTION

The invention is directed to a class of S-adenosyl homocysteine hydrolase (AHCY) inhibitors, their salts, pharmaceutical compositions comprising them and their use in therapy of the human body. In particular, the invention is directed to a class of AHCY inhibitors, and hence are useful in the treatment of diseases characterized by high homocysteine levels.

BACKGROUND OF THE INVENTION

S-adenosylhomocysteine, known as AdoHcy, is an intermediate in the metabolism of the sulfur-containing amino acids methionine and cysteine. AdoHcy is formed by the donation of a methyl group from S-adenosylmethionine (SAM) to biomolecules undergoing methylation reactions. AdoHcy is then metabolized by the enzyme S-adenosylhomocysteine hydrolase, known as AHCY or SAHH or SAH hydrolase, which reversibly hydrolyses AdoHcy to adenosine and homocysteine. Homocysteine can be remethylated back to methionine or undergo a series of metabolic steps leading to the biosynthesis of glutathione or cysteine. Following the hydrolysis of AdoHcy, homocysteine can also be secreted from the body or converted into the anti-oxidant, glutathione, by a series of transulfuration pathway reactions. Glutathione is a major anti-oxidant in the body. The relative ratio between oxidized and reduced forms of glutathione is thought to be an important indicator of oxidative state.

Furthermore, the ratio between SAM and AdoHcy is critical for many biological processes, as AdoHCY can inhibit many methyltransferases that use SAM as a methyl donor. Thus, the rate of conversion of AdoHcy to Hcy is a critical regulator of many biological reactions involving phospholipids, proteins, and nucleic acids. Various nucleosides and nucleoside derivatives act as inhibitors of AHCY. Chiang, *Pharmacol Ther* 1998, 77, 2, 115-134.

Homocysteine metabolism is also dependent on the nutrients folate, vitamin B12 and vitamin B6. Obeid et al, *FEBS Letters* 2006, 580:2994-3005. These nutrients are cofactors for the enzymes that remethylate Hcy back to methionine (folate, B12) or convert it to glutathione (B6).

AHCY is a 432 amino acid protein, which is a thioether hydrolase. AHCY is a cytosolic enzyme that has been found in a wide variety of cells. Walker, et al. *Can. J. Biochem.* 1975 53: 312-319. The sequence of AHCY is disclosed in International Patent Application Publication No. WO 2005/015221.

AHCY catalyzes the conversion of S-adenosyl-homocysteine to homocysteine and adenosine. Because of the key role of AdoHcy in the synthesis of cysteine, and the role of S-adenosylmethionine as a universal methyl donor, misregulation of AHCY can affect methylation of phosphlipids, proteins, DNA and RNA.

Epidemiological evidence demonstrates that increased levels of homocysteine are associated with many diseases, including cardiovascular disease, stroke, and neurodegenerative diseases such as Alzheimer's Disease. Hyperhomocysteinemia, which may be caused by folic acid deficiency, can contribute to Alzheimer's Disease. Morris, *Lancet Neurol.* 2003 2(7):425-8. Further, the known AHCY inhibitor 3-deaza-adenosine (DZA) has been shown to prevent oxidative damage and cognitive impairment in mice. Shea et al, *Neuromolecular Medicine* 2004, 5:173-182. In clinical studies, folate deficiency was associated with neurological disorders such as Alzheimer's disease. Ho et al., *Neurobiology of Disease,* 2003 14: 1, 32-42.

Seshadri et al, *N Engl. J Med,* 2002, 346:476-483, in a study of data from the Framingham Heart Study, found that increased homocysteine levels in plasma was an independent risk factor for dementia and Alzheimer's Disease. See also Morris, *Lancet Neurology* 2003, 2:425-428.

Hyperhomocysteinemia is a known risk factor for arterial vascular disease and venous thrombosis. Gellekink et al, *Eur J Hum Genet.* 2004 12(11):942-8; cardiovascular disease, Levine et al, *Prog Neuropsych Biol Psych* 2005, 29(7):1181-91; schizophrenia, Haidemenos et al, *Prog Neuropsychopharmacol Biol Psychiatry.* 2007 15; 31(6):1289-96; and bipolar disorder, Levine et al. Elevated homoscysteine levels have also been shown to be risk factors for stroke and Parkinson's Disease. Herrmann et al, *Fortschr Neurol Psychiatr.* 2007 75(9):515-27. Further, animal studies suggest that increased homocycsteine levels may be a factor in osteoporosis. Herrmann et al, *Clin. Chem.* 2007, 53(8):1455-61.

One possible method for treating diseases via the AHCY pathway is to develop mechanisms for clearing homocysteine from the body. For example, compounds or substances that increase the rate of vitamin B clearance of homocysteine in vivo may find utility as agents for treating disease associated with high levels of homocysteine. A second method of interfering with the AHCY pathway is to decrease production of homocytseine, i.e. to develop compounds that can inhibit production of homocysteine in vivo. For example, compounds or substances which inhibit AHCY may decrease the extent of hydrolysis of S-adenosyl homocysteine into homocysteine and adenosine.

The inventors have identified a novel group of compounds which act as inhibitors of S-adenosyl homocysteine hydrolase, thereby inhibiting the hydrolysis of S-adenosyl homocysteine into homocysteine and adenosine.

SUMMARY OF THE INVENTION

The present invention is directed to novel compounds of generic formula (I)

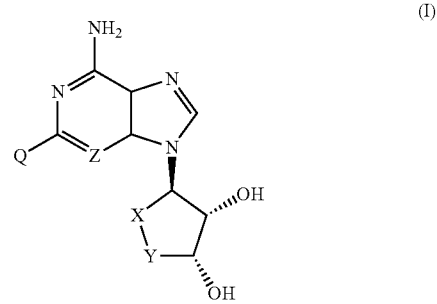

or pharmaceutically acceptable salts thereof, which are useful as AHCY inhibitors.

The invention is further directed to methods of treating a patient (preferably a human) for diseases or disorders which are characterized by high homocysteine levels, such as Alzheimer's disease, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

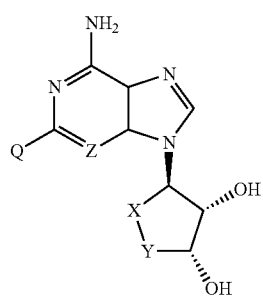

(I)

and pharmaceutically acceptable salts thereof, wherein
X—Y is selected from the group consisting of
(1) $CR^1R^2$—$CR^3R^4$,
(2) $CR^1$=$CR^2$;
Z is selected from the group consisting of
(1) —N—,
(2) —$CR^5$;
Q is selected from the group consisting of
(1) hydrogen,
(2) halogen, and
(3) —$C_{1-6}$ alkyl;
$R^1$, $R^2$, $R^3$ and $R^4$ are each independently selected from the group consisting of
(1) hydrogen,
(2) hydroxyl,
(3) halogen,
(4) —$C_{1-6}$ alkyl, wherein said alkyl is optionally substituted with
 (a) halogen, or
 (b) hydroxyl;
$R^5$ is selected from the group consisting of
(1) hydrogen,
(2) halogen,
(3) —$C_{1-6}$ alkyl, and
(4) —$C_{3-6}$ cycloalkyl.

In one embodiment, Z is N. In another embodiment, Z is —$CR^5$—, wherein $R^5$ is hydrogen, —$C_{1-3}$ alkyl (preferably methyl), or $R^5$— is halogen (preferably fluoro or chloro).

In one embodiment, X—Y is $CR^1R^2$—$CR^3R^4$.
In this embodiment, there is a sub-genus of compounds wherein each of $R^1$, $R^2$, $R^3$ and $R^4$ is selected from the group consisting of
(1) hydrogen, and
(2) —$C_{1-3}$ alkyl, wherein said alkyl is optionally substituted with
 (a) halogen, or
 (b) hydroxyl.
In another sub-genus, each of $R^1$, $R^2$, $R^3$ and $R^4$ is selected from the group consisting of
(1) hydrogen, and
(2) —$CH_2OH$.
In one embodiment, there is a sub-genus of compounds wherein $R^5$ is hydrogen. In another embodiment, $R^5$ is selected from the group consisting of
(1) halogen, and
(2) —$C_{1-3}$ alkyl, wherein said alkyl is optionally substituted with
 (a) halogen, or
 (b) hydroxyl.
In one embodiment, Q is selected from hydrogen and halogen (preferably fluoro). In particular embodiments, Q is hydrogen.
Typically, X—Y is $CH_2$—$CR^3R^4$, wherein each of $R^3$ and $R^4$ is selected from the group consisting of
(1) hydrogen, and
(2) —$C_{1-3}$ alkyl, wherein said alkyl is optionally substituted with
 (a) halogen, or
 (b) hydroxyl.
In particular embodiments, each of $R^1$, $R^2$, $R^3$ and $R^4$ is hydrogen (X—Y is $CH_2$—$CH_2$).
In another embodiment, X—Y is $CR^1$=$CR^2$.
In this embodiment, there is a sub-genus of compounds wherein each of $R^1$ and $R^2$ is selected from the group consisting of
(1) hydrogen, and
(2) —$C_{1-3}$ alkyl, wherein said alkyl is optionally substituted with
 (a) halogen, or
 (b) hydroxyl.
In another sub-genus, each of $R^1$ and $R^2$ is selected from the group consisting of
(1) hydrogen, and
(2) —$CH_2OH$.
Typically, X—Y is CH—$CR^2$, wherein $R^2$ is selected from the group consisting of
(1) hydrogen, and
(2) —$C_{1-3}$ alkyl, wherein said alkyl is optionally substituted with
 (a) halogen, or
 (b) hydroxyl.
Typically, X—Y is —CH=CH—.
In one embodiment, the invention is directed to methods of treating a patient (preferably a human) for diseases characterized by high homocysteine levels, such as Alzheimer's Disease, hypertension, cardiovascular disease, stroke, osteoporosis, Parkinson's Disease and schizophrenia, by administering to the patient a therapeutically effective amount of a compound of general formula (I).
The invention is also directed to the use of a compound of formula (I) for treating diseases or disorders characterized by high homocysteine levels, such as Alzheimer's disease, hypertension, cardiovascular disease, stroke, osteoporosis, Parkinson's Disease and schizophrenia.

The invention is also directed to medicaments or pharmaceutical compositions for treating diseases or disorders characterized by high homocysteine levels, such as Alzheimer's disease, hypertension, cardiovascular disease, stroke, osteoporosis, Parkinson's Disease and schizophrenia, which comprise a compound of formula (I), or a pharmaceutically acceptable salt thereof, and a pharmaceutically acceptable carrier.

The invention is further directed to a method for the manufacture of a medicament or a composition for treating diseases or disorders characterized by high homocysteine levels, such as Alzheimer's disease, hypertension, cardiovascular disease, stroke, osteoporosis, Parkinson's Disease or schizophrenia, comprising combining a compound of formula (I) with one or more pharmaceutically acceptable carriers.

Specific embodiments of formula (I) are described herein as exemplified compounds:

- (1R,2S,3R)-3-(4-amino-7-fluoro-1H-imidazo[4,5-c]pyridin-1-yl)cyclopentane-1,2-diol (1);
- (1R,2S,3R)-3-(4-amino-7-chloro-1H-imidazo[4,5-c]pyridin-1-yl)cyclopentane-1,2-diol(1-11);
- (1R,2S,3R)-3-(4-amino-7-methyl-1H-imidazo[4,5-c]pyridin-1-yl)cyclopentane-1,2-diol(1-12);
- (1R,2S,3R)-3-(6-amino-2-fluoro-9H-purin-9-yl)cyclopentane-1,2-diol(1-13);
- (1R,2S,3R)-3-(4-amino-6-fluoro-1H-imidazo[4,5-c]pyridin-1-yl)cyclopentane-1,2-diol(1-14);
- (1R,2S,3R)-3-(4-amino-6,7-difluoro-1H-imidazo[4,5-c]pyridin-1-yl)cyclopentane-1,2-diol(1-15);
- (1R,2S,3S)-3-(8-aminoimidazo[1,2-a]pyrazin-3-yl)cyclopentane-1,2-diol(2);
- (1S,2R,5R)-5-(4-amino-7-chloro-1H-imidazo[4,5-c]pyridin-1-yl)cyclopent-3-ene-1,2-diol(2-7);
- (1S,2R,5R)-5-(4-amino-7-methyl-1H-imidazo[4,5-c]pyridin-1-yl)cyclopent-3-ene-1,2-diol (2-8);
- (1S,2S,3S,4R)-4-(4-amino-7-fluoro-1H-imidazo[4,5-c]pyridin-1-yl)cyclopentane-1,2,3-triol(3);
- (1S,2S,3R,5S)-3-(4-amino-7-fluoro-1H-imidazo[4,5-c]pyridin-1-yl)-5-fluorocyclopentane-1,2-diol(4);
- (1R,2S,3S)-3-(4-amino-7-fluoro-1H-imidazo[4,5-c]pyridin-1-yl)-4-fluorocyclopentane-1,2-diol(5);
- (1R,2S,3R,5S)-3-(4-amino-7-fluoro-3a,7a-dihydro-1H-imidazo[4,5-c]pyridin-1-yl)-5-methylcyclopentane-1,2-diol (6);

and pharmaceutically acceptable salts thereof.

Where a variable occurs more than once in Formula (I) or in a substituent thereof, the individual occurrences of that variable are independent of each other, unless otherwise specified.

As used herein, in particular in the definitions of $R^1$, $R^2$, $R^3$ and $R^4$, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, in particular in the definition of Z, the term "cycloalkyl," by itself or as part of another substituent, means a saturated cyclic hydrocarbon radical having the number of carbon atoms designated (e.g., $C_{3-6}$ cycloalkyl means a cycloalkyl group having from three to six ring carbon atoms). Exemplary $C_{3-6}$ cycloalkyl groups for use in the invention include cyclopropyl, cyclobutyl, cyclopentyl and cyclohexyl.

As used herein, in particular in the definitions of Z, $R^1$, $R^2$, $R^3$ and $R^4$, the term "halo" or "halogen" includes fluoro, chloro, bromo and iodo. Preferred halogens for each of Z, $R^1$, $R^2$, $R^3$ and $R^4$, are fluoro and chloro, The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formula (I).

Formula (I) is shown above without a definite stereochemistry at the X—Y position. The present invention includes all stereoisomers of formula (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1991. The protecting groups may be removed at a convenient sequent stage using methods known from the art.

The compounds of the invention may also have utility as imaging agents. In this embodiment, the compounds of the invention can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lifes of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}$Tc, $^{201}$Tl and $^{123}$I.

In another embodiment, the compounds of the invention may be labeled with tritium (T or 3H), which is a radioactive isotope of hydrogen. The nucleus of tritium contains one proton and two neutrons. Methods of labeling with tritium are known to those of ordinary skill in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The radiolabeled compounds of the invention have utility in imaging AHCY or for diagnostic imaging with respect to any of the previously mentioned neurological and psychiatric disorders associated with AHCY.

Tritiated compounds of the invention may be useful in drug and/or tissue distribution studies and for measuring ACHY inhibitor enzyme occupancy.

Compounds which incorporate a radionuclide may be prepared by first synthesizing an unlabeled compound that optionally incorporates a halogen moiety or a double bond and then introducing an appropriate radionuclide using techniques well known in the art. Alternately, a radiolabeled compound of the invention may be prepared by alkylation with a radiolabeled alkylating agent.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

The present invention is directed to the use of the compounds of formula (I) disclosed herein as AHCY hydrolase inhibitors in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases characterized by high homocysteine levels, such as Alzheimer's disease. Other conditions that may be treated by the compounds of the invention include Parkinson's Disease, hypertension, schizophrenia, including the positive and negative symptoms of schizophrenia and treatment of cognitive impairment due to schizophrenia, bipolar disorder, cancer, cardiovascular disease, viral infections and osteoporosis.

In certain embodiments, the compounds of the invention are useful in treating Alzheimer's Disease. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketaniine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In one embodiment, the present invention provides a method for treating cognitive disorders, comprising: administering to a patient in need thereof an effective amount of a compound of the present invention. Particular cognitive disorders are dementia, delirium, amnesiac disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familialhypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

As stated above, the compounds of the invention may be used for treating stroke. One class of stroke patients to which a compound of the invention may be administered is a patient at risk for stroke. As used herein, the term "patient at risk for stroke" means an individual who has had a previous stroke, or has a risk factor for stroke. Known risk factors for stroke include atherosclerosis, arterial hypertension, lipohyalinosis, hyperlipidemia, hypercholesterolemia, atrial fibrillation, smoking, inflammatory markers (including C-reactive protein), infection, homocysteine, sleep-disordered breathing, cerebral autosomal dominant arteriopathy with subcortial infarcts and leuko-encephalopathy (CADASIL), migraine, sickle-cell anemia, antiphospholipid antibody syndrome, arterial dissection, cocaine abuse and obesity.

A second class of patients to which a compound of the invention may be administered are acute stroke patients, i.e., patients who have suffered ischemic stroke within the last 7 days. One preferred class of acute stroke patients are those who have suffered stroke within the last 3 days. A more preferred class of acute stroke patients are those who have suffered stroke within the last 48 hours, even more preferably within the last 24 hours. As common in the art of treating stroke, patients may be classified according to the period of time when stroke occurred. So, for example, one class of acute stroke patients are those who have suffered stroke within the last 18 hours. Another class of acute stroke patients are those who have suffered stroke within the last 12 hours. Another class of acute stroke patients are those who have suffered stroke within the last 8 hours. Another class of acute stroke patients are those who have suffered stroke within the last 6 hours. Another class of acute stroke patients are those who have suffered stroke within the last 4 hours. Another class of acute stroke patients are those who have suffered stroke within the last 3 hours.

A third class of patients to which a compound of the present invention may be administered are patients who have suffered stroke more than 7 days previously, who are typically in need of restorative treatment.

The compounds of the invention also have utility in the treatment of Parkinson's Disease, including primary parkinsonism, multiple system atrophy (MSA), progressive supranuclear palsy (PSP), corticobasal degeneration (CBD), dementia with Lewy bodies; Parkinsonism symptoms, including tremors, rigidity, bradykykinesia, akinesia and postural instability.

The compounds of the invention also have utility for reducing or inhibiting bone resorption, and for treating, reducing, inhibiting or preventing abnormal bone resorption, and conditions associated therewith. The compounds of the invention can thus be used in humans and other animals to increase bone mass and to prevent, inhibit, reduce and treat the following conditions and disease states: bone loss; osteoporosis, including but not limited to, post-menopausal osteoporosis, steroid-induced osteoporosis, male osteoporosis, disease-induced osteoporosis, idiopathic osteoporosis, and glucocorticoid-induced osteoporosis; osteonecrosis, Paget's disease; osteoarthritis; rheumatoid arthritis, other arthritic conditions, abnormally increased bone turnover; localized bone loss associated with periprosthetic bone loss or osteolysis; bone fractures; metastatic bone disease; Gaucher's disease; avascular necrosis; polyostotic fibrous dysplasia; Charcot's joint; parasitic disorders; osteogenesis imperfecta; homocystinuria; lysinuric protein intolerance; Turner's syndrome; immobilization; fibrous dysplasia ossificans progressive; fibrogenesis imperfecta ossium; periodontal disease; tooth loss; hypercalcemia of malignancy; multiple myeloma; osteopenia, including but not limited to, immobilization-induced osteopenia and osteopenia due to bone metastases; and other bone diseases and conditions that may be associated with abnormal bone resorption.

The subject or patient to whom the compounds of the present invention is administered is generally a human being, male or female, characterized by high homocysteine, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinis agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of other active ingredients that may be administered in combination with a composition of the present invention, and either administered separately or in the same pharmaceutical composition, include agents for the treatment of diabetic conditions, such as (a) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, and TAK-559; PPARα agonists, such as fenofibric acid derivatives (gemfibrozil, clofibrate, fenofibrate and bezafibrate); and selective PPARγ modulators (SPPARγM's), such as disclosed in WO 02/060388, WO 02/08188, WO 2004/019869, WO 2004/020409, WO 2004/020408, and WO 2004/066963; (ii) biguanides, such as metformin and phenformin, and (iii) protein tyrosine phosphatase-1B (PTP-1B) inhibitors;

(b) insulin or insulin mimetics;

(c) sulfonylureas and other insulin secretagogues, such as tolbutamide, glyburide, glipizide, glimepiride, and meglitinides, such as nateglinide and repaglinide;

(d) α-glucosidase inhibitors (such as acarbose and miglitol);

(e) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(f) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(g) GIP and GIP mimetics, such as those disclosed in WO 00/58360, and GIP receptor agonists;

(h) PACAP, PACAP mimetics, and PACAP receptor agonists such as those disclosed in WO 01/23420;

(i) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists, such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(j) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(k) anti-obesity compounds, such as fenfluramine, dexfenfluramine, phentermine, sibutramine, orlistat, neuropeptide Y1 or Y5 antagonists, β3 adrenergic receptor agonists, melanocortin-receptor agonists, in particular melanocortin-4 receptor agonists, ghrelin antagonists, bombesin receptor agonists (such as bombesin receptor subtype-3 agonists), a cannabinoid CB1 receptor antagonist/inverse agonist, 5-HT (serotonin) inhibitors, and melanin-concentrating hormone (MCH) receptor antagonists;

(l) ileal bile acid transporter inhibitors;

(m) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(n) antihypertensive agents, such as neutral endopeptidase inhibitors (e.g., thiorphan and phosphoramidon), aldosterone antagonists, renin inhibitors (e.g. enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, and peripheral vasodilators (e.g. hydralazine);

(o) glucokinase activators (GKAs), such as those disclosed in WO 03/015774; WO 04/076420; and WO 04/081001;
(p) inhibitors of 11β-hydroxysteroid dehydrogenase Type 1, such as those disclosed in U.S. Pat. No. 6,730,690; WO 03/104207; and WO 04/058741;
(q) inhibitors of cholesteryl ester transfer protein (CETP), such as torcetrapib; and
(r) inhibitors of fructose 1,6-bisphosphatase, such as those disclosed in U.S. Pat. Nos. 6,054,587; 6,110,903; 6,284, 748; 6,399,782; and 6,489,476.
(s) dipeptidyl peptidase IV (DP-IV) inhibitors;
(t) PPARδ agonists such as those disclosed in WO97/28149; and
(u) agents intended for use in inflammatory conditions such as aspirin, non-steroidal anti-inflammatory drugs, glucocorticoids, azulfidine, and cyclo-oxygenase 2 selective inhibitors, including etoricoxib and rofecoxib.

Examples of anti-hypertensive agents that can be used in combination with the compounds of the invention include angiotensin II receptor antagonists (for example losartan, candesartan, irbesartan, valsartan, telmisartan, and eprosartan, including all stereoisomers, pharmaceutically acceptable salts, hydrates, and crystalline forms thereof.), ACE inhibitors (for example, alacepril, benazepril, captopril, ceronapril, cilazapril, delapril, enalapril, enalaprilat, fosinopril, imidapril, lisinopril, moveltipril, moexipril, perindopril, quinapril, ramipril, spirapril, temocapril, and trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholytics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, and peripheral vasodilators (e.g. hydralazine).

Examples of agents for treating schizophrenia that can be used in combination with the compounds of the invention include sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoetamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

Alternatively, the compounds of the invention may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

The compounds of the invention may also be used in combination with phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. The subject compound may be used in combination with acetophenazine, alentemol, aripiprazole, amisuipride, benzhexol, bromocriptine, biperiden, chiorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Further, the compounds of the invention may be used in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRTs), corticotropin releasing factor (CRF) antagonists, a-adrenoreceptor antagonists, neurokinin-1 receptor antagonists, atypical anti-depressants, benzodiazepines, 5-HT1A agonists or antagonists, especially S-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide; venlafaxine; duloxetine; aprepitant; bupropion, lithium, nefazodone, trazodone and viloxazine; alprazolam, chlordiazepoxide, clonazepam, chiorazepate, diazepam, halazepam, lorazepam, oxazepam and prazepam; buspirone, flesinoxan, gepirone and ipsapirone, and pharmaceutically acceptable salts thereof.

The compounds of the invention may also be useful in combination with anti-Parkinson's agents, such as 1-dopa, dopa decarboxylase inhibitors, including carbidopa, levodopa, benserazide, combination preparations of carbidopa/levodopa (e.g. SINEMET, PARCOPA), benserazide/levodopa (e.g. MADOPAR); carbidopa/levodopa/entacapone (STALEVO); COMT inhibitors, such as entacapone (COMTAN) and tolcapone (TASMAR); dopamine agonists, such as bromocriptine (PARLODEL), pergolide (PERMAX), pramipexole (MIRAPEX), rotigotine transdermal (NEUPRO), ropinirole (REQUIP), cabergoline, apomorphine (APOKYN), and lisuride; dopamine agonists; MAO-B inhibitors, such as rasagiline (AZILECT), selegiline (EL-DEPRYL, CARBEX, DEPRENYL), benzotropine mesylate (COGENTIN), metabolites of selegiline (L-amphetamine and L-methamphetamine), amantadine (SYMMETREL) and trihexyphenyl (ARTANE).

The compounds of the invention may also be used in combination with agents for treatment of osteoporosis or related diseases. For the treatment and prevention of osteoporosis, the compounds of the present invention can be administered in combination with at least one bone-strengthening agent selected from antiresorptive agents, osteoanabolic agents, and other agents beneficial for the skeleton through mechanisms which are not precisely defined, such as calcium supplements, flavonoids, and vitamin D analogs. The conditions of periodontal disease, bone fracture, and bone damage following bone reconstructive surgery can also benefit from these combined treatments. For example, the compounds of the invention can be effectively administered in combination with effective amounts of other agents such as estrogens, bisphosphonates, SERMs, cathepsin K inhibitors, .alpha β3 integrin receptor antagonists, vacuolar ATPase inhibitors, the polypeptide osteoprotegerin, antagonists of VEGF, thiazolidinediones, calcitonin, protein kinase inhibitors, parathyroid hormone (PTH) and analogs, calcium receptor antagonists, growth hormone secretagogues, growth hormone releasing hormone, insulin-like growth factor, bone morphogenetic protein (BMP), inhibitors of BMP antagonism, prostaglandin derivatives, fibroblast growth factors, vitamin D and derivatives thereof, vitamin K and derivatives thereof, soy isoflavones, calcium salts, and fluoride salts.

In one embodiment of the present invention, a compound of the instant invention can be effectively administered in combination with an effective amount of at least one bone-strengthening agent chosen from estrogen, and estrogen derivatives, alone or in combination with progestin or progestin derivatives; bisphosphonates; antiestrogens or selective estrogen receptor modulators; alpha β3 integrin receptor antagonists; cathepsin K inhibitors; osteoclast vacuolar ATPase inhibitors; calcitonin; and osteoprotegerin.

Non-limiting representatives of estrogen and estrogen derivatives include steroidal compounds having estrogenic activity such as, for example, 17 β-estradiol, estrone, conjugated estrogen (PREMARIN), equine estrogen, 17 β-ethynyl estradiol, and the like. The estrogen or estrogen derivative can be employed alone or in combination with a progestin or progestin derivative. Nonlimiting examples of progestin derivatives are norethindrone and medroxy-progesterone acetate.

Non-limiting examples of bisphosphonate compounds which can also be employed in combination with a compound of the present invention include:

(a) alendronate (also known as alendronic acid, 4-amino-1-hydroxybutylidene-1,1-bisphosphonic acid, alendronate sodium, alendronate monosodium trihydrate or 4-amino-1-hydroxybutylidene-1,1-bisphosphonic acid monosodium trihydrate;

(b) [(cycloheptylamino)-methylene]-bis-phosphonate (incadronate);

(c) (dichloromethylene)-bis-phosphonic acid (clodronic acid) and the disodium salt (clodronate);

(d) [1-hydroxy-3-(1-pynrolidinyl)-propylidene]-bis-phosphonate;

(e) (1-hydroxyethylidene)-bis-phosphonate (etidronate);

(f) [1-hydroxy-3-(methylpentylamino)propylidene]-bis-phosphonate (ibandronate);

(g) (6-amino-1-hydroxyhexylidene)-bis-phosphonate (neridronate);

(h) [3-(dimethylamino)-1-hydroxypropylidene]-bis-phosphonate (olpadronate);

(i) (3-amino-1-hydroxypropylidene)-bis-phosphonate (pamidronate);

(j) [2-(2-pyridinyl)ethylidene]-bis-phosphonate (piridronate);

(k) [1-hydroxy-2-(3-pyridinyl)-ethylidene]-bis-phosphonate (risedronate);

(l) {[(4-chlorophenyl)thio]methylene}-bis-phosphonate (tiludronate);

(m) [1-hydroxy-2-(1H-imidazol-1-yl)ethylidene]-bis-phosphonate (zoledronate); and [0273](n) [1-hydroxy-2-imidazopyridin-(1,2-a)-3-ylethylidene]-bis-phosphonate (minodronate).

Still further, antiestrogenic compounds such as raloxifene, clomiphene, zuclomiphene, enclomiphene, nafoxidene, CI-680, CI-628, CN-55,945-27, Mer-25, U-11,555A, U-100A, and salts thereof, and the like (see, e.g., U.S. Pat. Nos. 4,729,999 and 4,894,373) can be used in combination with a compound of the invention. These agents are also known as SERMs, or selective estrogen receptor modulators, agents known in the art to prevent bone loss by inhibiting bone resorption via pathways believed to be similar to those of estrogens. Non-limiting representatives of SERMs include, for example, tamoxifen, raloxifene, lasofoxifene, toremifene, azorxifene, EM-800, EM-652, TSE 424, clomiphene, droloxifene, idoxifene, and levormeloxifene [Goldstein, et al., "A pharmacological review of selective estrogen receptor modulators," Human Reproduction Update, 6: 212-224 (2000); Lufkin, et al., Rheumatic Disease Clinics of North America, 27: 163-185 (2001), and "Targeting the Estrogen Receptor with SERMs," Ann. Rep. Med. Chem. 36: 149-158 (2001)].

Alpha β3 Integrin receptor antagonists suppress bone resorption and can be employed in combination with the SARMs of structural formula I for the treatment of bone disorders including osteoporosis. Peptidyl as well as peptidomimetic antagonists of the alpha β3 integrin receptor have been described both in the scientific and patent literature. For example, reference is made to W. J. Hoekstra and B. L. Poulter, Curr. Med. Chem. 5: 195-204 (1998) and references cited therein.

Members of the class of HMG-CoA reductase inhibitors, known as the "statins," have been found to trigger the growth of new bone, replacing bone mass lost as a result of osteoporosis. Therefore, the statins hold promise for the treatment of bone resorption. Examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; cerivastatin, particularly the sodium salt thereof, rosuvastatin, and pitavastatin, also referred to as NK-104, itavastatin, or nisvastatin.

Activators of the peroxisome proliferator-activated receptor-.gamma. (PPAR.gamma.), such as the thiazolidinediones (TZD's), inhibit osteoclast-like cell formation and bone resorption in vitro. Results reported by R. Okazaki et al. in Endocrinology, 140: 5060-5065 (1999) point to a local mechanism on bone marrow cells as well as a systemic one on glucose metabolism. Nonlimiting examples of PPAR gamma activators include the glitazones, such as troglitazone, pioglitazone, rosiglitazone, and BRL 49653.

Osteoanabolic agents are those agents that are known to build bone by increasing the production of the bone protein matrix. Such osteoanabolic agents include, for example, parathyroid hormone (PTH) and fragments thereof, such as naturally occurring PTH (1-84), PTH (1-34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery*, Vol. 3, No. 8, 2000). An injectable recombinant form of human PTH, Forteo (teriparatide), has received regulatory approval in the U.S. for the treatment of osteoporosis.

Insulin-like growth factor (IGF) can also be used together with the compounds of the invention. Insulin-like growth factors can be selected from Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., Principles of Bone Biology, San Diego: Academic Press; and Ghiron et al., J. Bone Miner. Res. 10: 1844-1852 (1995)].

Inhibitors of BMP antagonism can also be used together with the compounds of the invention. In one embodiment, BMP antagonist inhibitors are chosen from inhibitors of the BMP antagonists SOST, noggin, chordin, gremlin, and dan [see Massague and Chen, "Controlling TGF-beta signaling," Genes Dev., 14: 627-644, 2000; Aspenberg et al., J. Bone Miner. Res. 16: 497-500, 2001; and Brunkow et al., Am. J. Hum. Genet. 68: 577-89 (2001)].

The tissue-selective androgen receptor modulators of the present invention can also be combined with the polypeptide osteoprotegerin for the treatment of conditions associated with bone loss, such as osteoporosis. The osteoprotegerin can be selected from mammalian osteoprotegerin and human osteoprotegerin. The polypeptide osteoprotegerin, a member of the tumor necrosis factor receptor super-family, is useful to treat bone diseases characterized by increased bone loss, such as osteoporosis.

In addition to bone resorption inhibitors and osteoanabolic agents, there are also other agents known to be beneficial for the skeleton through mechanisms which are not precisely defined. These agents can also be favorably combined with the compounds of the invention. These include Vitamin D, vitamin D derivatives and analogs, including, for example, Vitamin K and Vitamin K derivatives, including menatetrenone (vitamin K2) [see Shiraki et al., J. Bone Miner. Res., 15: 515-521 (2000)]; soy isoflavones, including ipriflavone; fluoride salts, including sodium fluoride (NaF) and monosodium fluorophosphate (MFP); dietary calcium supplements, including calcium carbonate, calcium citrate, and natural calcium salts.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a faun suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage fowls.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention may be prepared according to the following reaction schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

Certain of the starting materials are described in Gallos, J. K. et al, *J. Org. Chem.;* 2005; 70(17); 6884-6890, Choi, W. J., et al, *J. Org. Chem.;* 2004; 69(7); 2634-2636, and Moon, Won Jun Choi, et al, *Tetrahedron Asymmetry,* 13 (11), 1189-1193.

The following examples are provided to illustrate the invention and are not to be construed as limiting the scope of the invention in any manner.

General Synthetic Scheme

According to the general synthetic scheme below, appropriately substituted and/or protected unsaturated alcohols A-1 can be hydrogenated to produce both ketones A-2 and alcohols A-3. Ketone A-2 can be reduced to the corresponding alcohol A-3 using sodium borohydride. Here X—Y is unsaturated for alcohol A-1 (as in X═Y) and substituted according to the above generic description of compounds of formula (I)

Alcohol A-3 is then coupled with 4-fluoro-inaidazopyridines A-4 via Mitsunobu conditions to provide a regioisomeric mixture of A-5 and A-6. Here X—Y can be either saturated (as in X—Y) or unsaturated (as in X═Y) and substituted according to the above generic description of compounds of formula (I) Here Z can also be substituted according to the above generic description of compounds of formula (I).

4-Fluoro-imidazopyridines A-5 and A-6 are then regio selectively reacted with ammonia under thermal conditions to yield 4-amino-imidazopyridines A-7 and A-8.

Subsequent deprotection may vary depending on the nature of the X—Y substitution, but acid hydrolysis is utilized to remove the ketal group to provide final compounds A-9 and A-10.

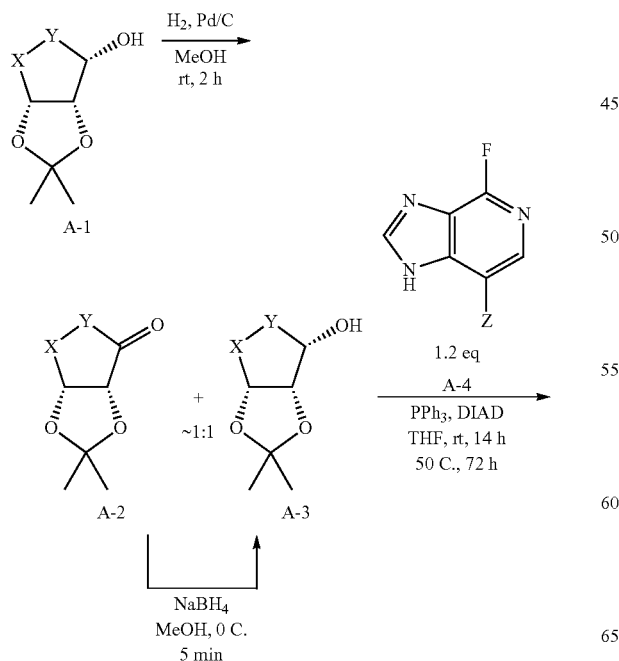

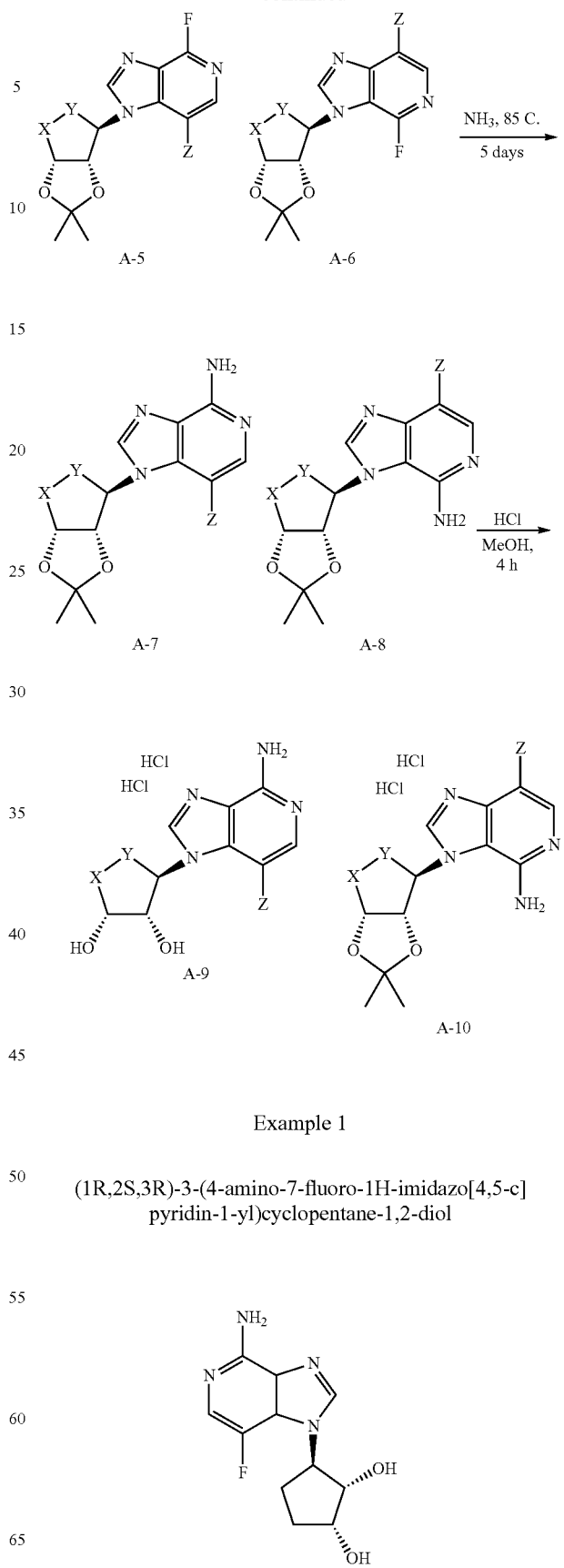

Example 1

(1R,2S,3R)-3-(4-amino-7-fluoro-1H-imidazo[4,5-c]pyridin-1-yl)cyclopentane-1,2-diol

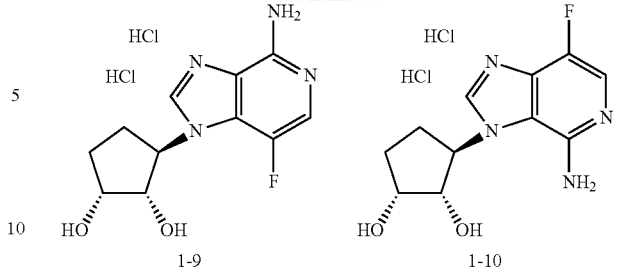

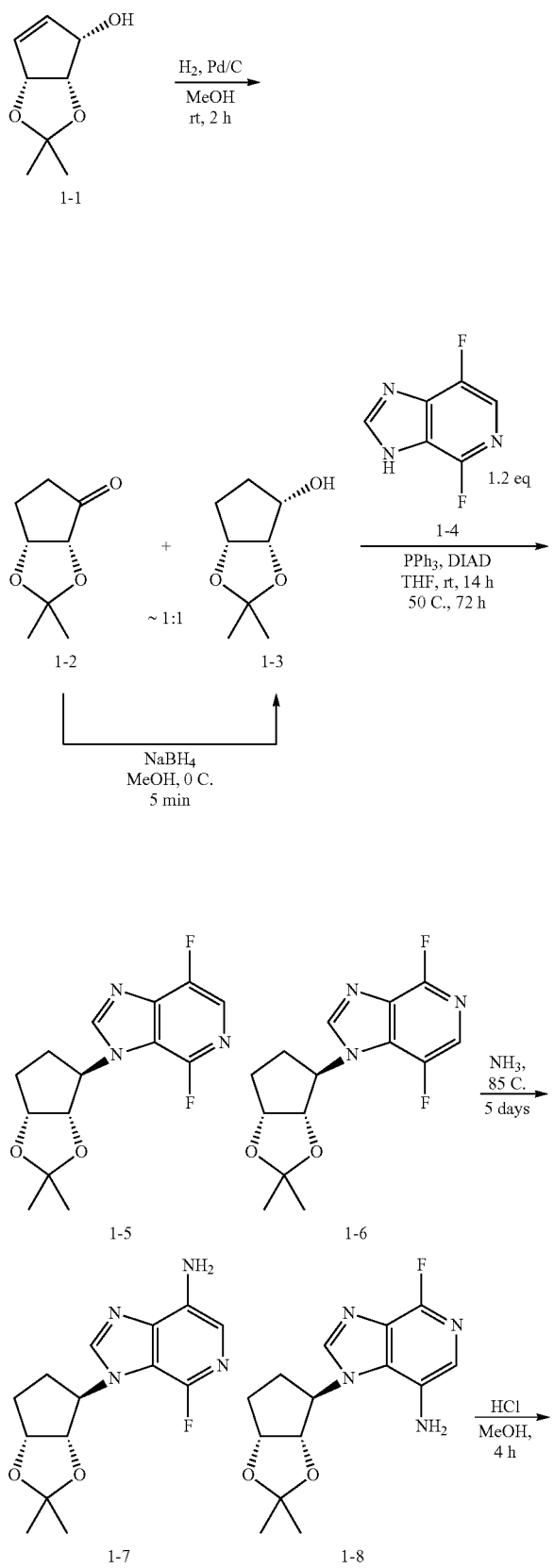

(3aR,6aR)-2,2-dimethyldihydro-3aH-cyclopenta[d][1,3]dioxol-4(5H)-one (1-2)

(3aS,4S,6aR)-2,2-dimethyl-4,6a-dihydro-3aH-cyclopenta[d][1,3]dioxol-4-ol (1-1) (10 g, 64.0 mmol, 1 equiv) was dissolved in MeOH (200 mL), the system was placed under nitrogen and 10% Pd/C (681 mg, 6.4 mmol, 0.1 equiv) was carefully added. The resulting mixture was stirred under a $H_2$ atmosphere (1 atm) until disappearance of the starting material as monitored by LC-MS analysis. Hydrogen was removed followed by filtration through a celite plug and washing of the solids with MeOH (4×75 mL). The filtrate was concentrated and the residue was purified via flash chromatography on a 120 g silica gel column (gradient elution 0 to 50% ethyl acetate in hexanes) to yield (3aR,6aR)-2,2-dimethyldihydro-3aH-cyclopenta[d][1,3]dioxol-4(5H)-one (1-2) as a white fluffy solid and (3aS,4S,6aR)-2,2-dimethyltetrahydro-3aH-cyclopenta[d][1,3]dioxol-4-ol (1-3) as a colorless oil. $^1$H NMR (1-2) (500 MHz, CDCl$_3$): δ 4.84 (t, J=4.8 Hz, 1H); 4.19 (d, J=5.2 Hz, 1H); 2.65-2.53 (m, 1H); 2.33-2.23 (m, 2H); 2.11-2.01 (m, 1H); 1.43 (s, 3H); 1.38-1.31 (m, 3 H). $^1$H NMR (1-3) (400 MHz, CDCl$_3$): δ 4.61 (t, J=5.3 Hz, 1H); 4.40 (t, J=5.6 Hz, 1H); 3.88-3.77 (m, 1H); 2.43 (d, J=9.9 Hz, 1H); 1.93-1.75 (m, 2H); 1.70-1.55 (m, 1H); 1.49 (s, 3H); 1.47-1.35 (m, 1H); 1.34 (s, 3H).

(3aS,4S,6aR)-2,2-dimethyltetrahydro-3aH-cyclopenta[d][1,3]dioxol-4-ol (1-3)

(3aR,6aR)-2,2-dimethyldihydro-3aH-cyclopenta[d][1,3]dioxol-4(5H)-one (1-2) (2.75 g, 17.6 mmol, 1 equiv) was dissolved in methanol (166 mL) and sodium borohydride (1.0 g, 26.4 mmol, 1.5 equiv) was added portion wise at 0° C. Upon disappearance of the starting material as monitored by LC-MS analysis, water was added and the mixture was concentrated. The aqueous phase was extracted with DCM (3×100 mL), the combined organics were dried (Na$_2$SO$_4$), and the solvent was removed to afford (3AS,4S,6aR)-2,2-dimethyltetrahydro-3aH-cyclopenta[d][1,3]dioxol-4-ol (1-3) as a colorless oil that did not require further purification.

1-[(3aS,4R,6aR)-2,2-dimethyltetrahydro-3aH-cyclopenta[d][1,3]dioxol-4-yl]-4,7-difluoro-1H-imidazo[4,5-c]pyridine (1-6)

(3aS,4S,6aR)-2,2-dimethyltetrahydro-3aH-cyclopenta[d][1,3]dioxol-4-ol (1-3) (4.3 g, 27.2 mmol, 1 equiv) was dissolved in dry THF (136 mL). Triphenylphosphine (10.7 g, 40.8 mmol, 1.5 equiv) was added, followed by 4,7-difluoro-1H-imidazo[4,5-c]pyridine (1-4, 5.1 g, 32.6 mmol, 1.2 equiv). The mixture was cooled to 0° C. and DIAD (7.9 mL, 40.8 mmol, 1.5 equiv) was added dropwise. The resulting mixture was stirred at ambient temperature for 14 hours and then heated to 50° C. for an additional 72 hours. The solvent was removed at reduced pressure and the yellow residue was purified via flash chromatography on 2-330 g silica gel columns (gradient elution 0 to 100% ethyl acetate in hexanes) to yield 1-[(3aS,4R,6aR)-2,2-dimethyltetrahydro-3aH-cyclopenta[d][1,3]dioxol-4-yl]-4,7-difluoro-1H-imidazo[4,5-c]pyridine (1-6) and 3-((3aS,4R,6aR)-2,2-dimethyltetrahydro-3aH-cyclopenta[d][1,3]dioxol-4-yl)-4,7-difluoro-3H-imidazo[4,5-c]pyridine (1-5) as a 1:1 regioisomeric mixture. $^1$H NMR (1-6) (500 MHz, CDCl$_3$): δ 7.85 (m, 2H); 5.00 (brs, 1H); 4.90 (t, J=5.6 Hz, 1H); 4.82 (t, J=7.3 Hz, 1H); 2.56 (m, 1H); 2.04-2.19 (m, 3H); 1.55 (s, 3H); 1.34 (s, 3H). LRMS m/z (M+H) 296.0 found, 296.1 required. $^1$H NMR (1-5) (500 MHz, CDCl$_3$): δ 7.92 (s, 1H); 7.82 (m, 1H); 5.00 (brs, 1H); 4.90 (t, J=5.6 Hz, 1H); 4.82 (t, J=7.3 Hz, 1H); 2.56 (m, 1H); 2.04-2.19 (m, 3H); 1.55 (s, 3H); 1.34 (s, 3H). LRMS m/z (M+H) 296.0 found, 296.1 required.

1-[(3aS,4R,6aR)-2,2-dimethyltetrahydro-3aH-cyclopenta[d][1,3]dioxol-4-yl]-7-fluoro-1H-imidazo[4,5-c]pyridin-4-amine (1-7)

Liquid ammonia (200 mL) was added to a mixture of 1-[(3aS,4R,6aR)-2,2-dimethyltetrahydro-3aH-cyclopenta[d][1,3]dioxol-4-yl]-4,7-difluoro-1H-imidazo[4,5-c]pyridine (1-6) (2.4 g, 8.1 mmol, 1 equiv) and 3-[(3aS,4R,6aR)-2,2-dimethyltetrahydro-3aH-cyclopenta[d][1,3]dioxol-4-yl]-4,7-difluoro-3H-imidazo[4,5-c]pyridine (1-5) (2.5 g, 8.5 mmol, 1 equiv). The resulting solution was heated in a high pressure vessel to 85° C. for 5 days. The mixture was then concentrated and purified via flash chromatography on a 120 g silica gel column (gradient elution 0 to 100% ethyl acetate in dichloromethane and then 100% methanol to elute 1-7) to yield 1-[(3aS,4R,6aR)-2,2-dimethyltetrahydro-3aH-cyclopenta[d][1,3]dioxol-4-yl]-7-fluoro-1H-imidazo[4,5-c]pyridin-4-amine (1-7) as a tan solid in addition to 3-[(3aS,4R,6aR)-2,2-dimethyltetrahydro-3aH-cyclopenta[d][1,3]dioxol-4-yl]-7-fluoro-3H-imidazo[4,5-c]pyridin-4-amine (1-8) and recovered starting material 1-5. $^1$H NMR (1-7) (500 MHz, CD$_3$OD): δ 8.13 (s, 1H); 7.62 (d, J=3.7 Hz, 1H); 4.95-4.87 (m, 3H); 2.52-2.42 (m, 1H); 2.21-1.99 (m, 3H); 1.50 (s, 3H); 1.33 (s, 3H). LRMS m/z (M+H) 293.0 found, 293.1 required. $^1$H NMR (1-8) (500 MHz, CDCl$_3$): δ 7.86-7.81 (m, 1H); 7.76-7.73 (m, 1H); 5.07 (s, 1H); 5.01 (s, 2H); 4.87 (t, J=4.6 Hz, 1H); 4.62 (d, J=6.2 Hz, 1H); 2.66-2.57 (m, 1H); 2.46-2.38 (m, 1H); 2.24-2.17 (m, 2H); 1.57 (s, 3H); 1.35-1.30 (m, 3H). LRMS m/z (M+H) 293.0 found, 293.1 required.

(1R,2S,3R)-3-(4-amino-7-fluoro-1H-imidazo[4,5-c]pyridin-1-yl)cyclopentane-1,2-diol (1-9)

Concentrated HCl (5 mL) was added to 1-((3aS,4R,6aR)-2,2-dimethyltetrahydro-3aH-cyclopenta[d][1,3]dioxol-4-yl)-7-fluoro-1H-imidazo[4,5-c]pyridin-4-amine (1-7) (2.3 g, 7.9 mmol, 1 equiv) in methanol (60 mL). After disappearance of the starting material as monitored by LC-MS analysis, the mixture was concentrated to afford (1R,2S,3R)-3-(4-amino-7-fluoro-1H-imidazo[4,5-c]pyridin-1-yl)cyclopentane-1,2-diol (1-9) as a tan solid of the bis-HCl salt. $^1$H NMR (1-9) (500 MHz, DMSO): δ 8.76 (s, 1H); 8.55 (s, 2H); 8.03 (d, J=5.5 Hz, 1H); 4.88 (q, J=9.3 Hz, 1H); 4.19 (dd, J=9.4, 4.0 Hz, 1H); 4.00 (t, J=4.5 Hz, 1H); 2.41-2.31 (m, 1H); 2.15-2.06 (m, 1H); 1.92-1.83 (m, 1H); 1.66 (ddd, J=14.0, 9.7, 4.9 Hz, 1H). HRMS m/z (M+H) 253.1093 found, 253.1095 required. $^1$H NMR (1-10) (500 MHz, DMSO): δ 8.95 (s, 1H); 8.14 (s, 2H); 8.06 (d, J=4.5 Hz, 1H); 4.96 (q, J=8.4 Hz, 1H); 4.10 (dd, J=8.7, 4.8 Hz, 1H); 4.02 (d, J=4.4 Hz, 1H); 2.38-2.29 (m, 1H); 2.20-2.11 (m, 2H); 1.72-1.65 (m, 1H). HRMS m/z (M+H) 253.1095 found, 253.1095 required.

Additional compounds 1-11 to 1-15 were synthesized, using the synthetic scheme described above for Example 1 with appropriate modifications within the knowledge of one skilled in the art.

| | Structure | Name | Mass |
|---|---|---|---|
| 1-11 | (structure with NH$_2$, Cl, cyclopentane-diol) | (1R,2S,3R)-3-(4-amino-7-chloro-1H-imidazo[4,5-c]pyridin-1-yl)cyclopentane-1,2-diol | HRMS m/z (M + H) 269.0800 found, 269.0802 required. |
| 1-12 | (structure with NH$_2$, CH$_3$, cyclopentane-diol) | (1R,2S,3R)-3-(4-amino-7-methyl-1H-imidazo[4,5-c]pyridin-1-yl)cyclopentane-1,2-diol | LRMS m/z (M + H) 249.0 found, 249.1 required. |
| 1-13 | (structure with NH$_2$, F, purine, cyclopentane-diol) | (1R,2S,3R)-3-(6-amino-2-fluoro-9H-purin-9-yl)cyclopentane-1,2-diol | LRMS m/z (M + H) 253.9 found, 254.1 required. |
| 1-14 | (structure with NH$_2$, F, cyclopentane-diol) | (1R,2S,3R)-3-(4-amino-6-fluoro-1H-imidazo[4,5-c]pyridin-1-yl)cyclopentane-1,2-diol | LRMS m/z (M + H) 252.9 found, 253.1 required. |
| 1-15 | (structure with NH$_2$, F, F, cyclopentane-diol) | (1R,2S,3R)-3-(4-amino-6,7-difluoro-1H-imidazo[4,5-c]pyridin-1-yl)cyclopentane-1,2-diol | LRMS m/z (M + H) 270.9 found, 271.1 required. |

Example 2

(1R,2S,3S)-3-(8-aminoimidazo[1,2-a]pyrazin-3-yl)cyclopentane-1,2-diol

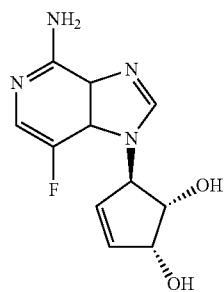

SYNTHETIC SCHEME

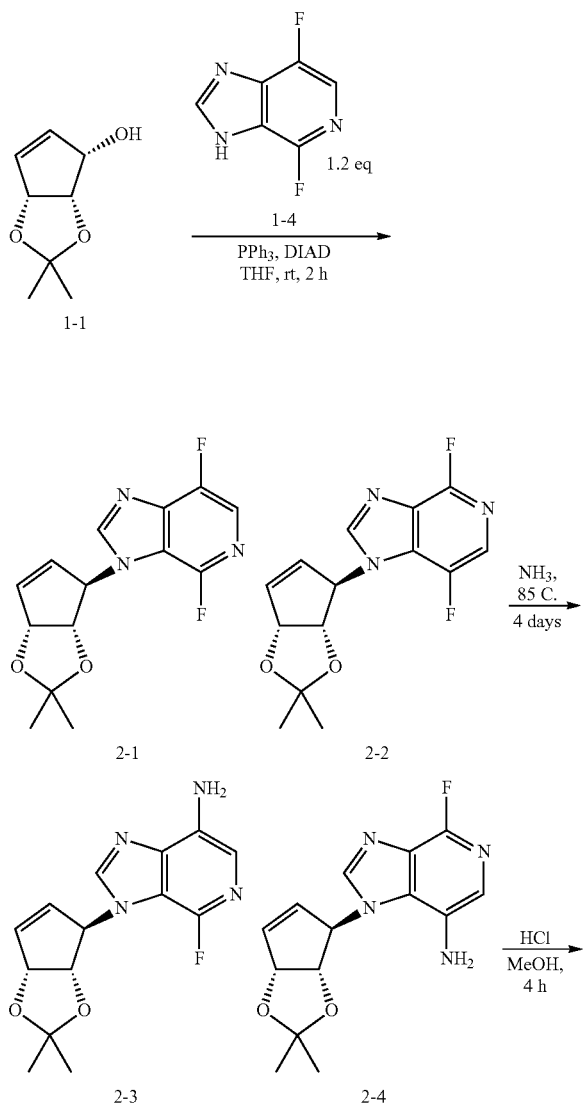

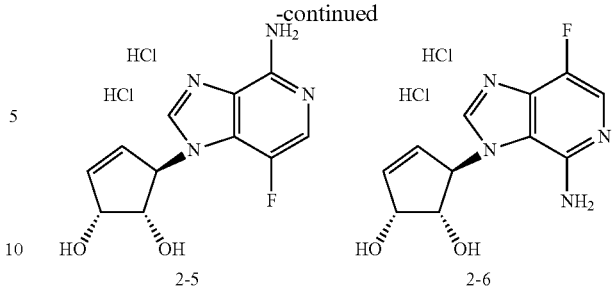

1-[(3aS,4R,6aR)-2,2-dimethyl-4,6a-dihydro-3aH-cyclopenta[d][1,3]dioxol-4-yl]-4,7-difluoro-1H-imidazo[4,5-c]pyridine (2-2)

(3aS,4S,6aR)-2,2-dimethyl-4,6a-dihydro-3aH-cyclopenta[d][1,3]dioxol-4-ol (1-1) (250 mg, 1.6 mmol, 1 equiv) was dissolved in dry THF (8 mL). Triphenylphosphine (630 mg, 2.4 mmol, 1.5 equiv) was added, followed by 4,7-difluoro-1H-imidazo[4,5-c]pyridine (1-4, 300 mg, 1.9 mmol, 1.2 equiv). The mixture was cooled to 0° C. and DIAD (470 μL, 2.4 mmol, 1.5 equiv) was added dropwise. The resulting mixture was stirred at ambient temperature for 2 hours. The solvent was removed at reduced pressure and the yellow residue was purified via flash chromatography on a 80 g silica gel column (gradient elution 0 to 100% ethyl acetate in hexanes) to yield 1-[(3aS,4R,6aR)-2,2-dimethyl-4,6a-dihydro-3aH-cyclopenta[d][1,3]dioxol-4-yl]-4,7-difluoro-1H-imidazo[4,5-c]pyridine (2-2) and 3-[(3aS,4R,6aR)-2,2-dimethyl-4,6a-dihydro-3aH-cyclopenta[d][1,3]dioxol-4-yl]-4,7-difluoro-3H-imidazo[4,5-c]pyridine (2-1) as a 1:1 regioisomeric mixture. $^1$H NMR (2-2) (500 MHz, CDCl$_3$): δ 7.82 (s, 1H); 7.86 (m, 1H); 6.42 (d, J=5.7 Hz, 1H); 6.05 (s, 1H); 5.75 (s, 1H); 5.44 (d, J=5.5 Hz, 1H); 4.68 (d, J=5.7 Hz, 1H); 1.51 (s, 3H); 1.37 (s, 3H). LRMS m/z (M+H) 294.0 found, 294.1 required. $^1$H NMR (2-1) (500 MHz, CDCl$_3$): δ 7.90 (s, 1H); 7.84 (m, 1H); 6.42 (d, J=5.7 Hz, 1H); 6.05 (s, 1H); 5.75 (s, 1H); 5.44 (d, J=5.5 Hz, 1H); 4.68 (d, J=5.7 Hz, 1H); 1.51 (s, 3H); 1.37 (s, 3H). LRMS m/z (M+H) 294.0 found, 294.1 required.

1-[(3aS,4R,6aR)-2,2-dimethyl-4,6a-dihydro-3aH-cyclopenta[d][1,3]dioxol-4-yl]-7-fluoro-1H-imidazo[4,5-c]pyridin-4-amine (2-3)

Liquid ammonia (30 mL) was added to a mixture of 1-[(3aS,4R,6aR)-2,2-dimethyl-4,6a-dihydro-3aH-cyclopenta[d][1,3]dioxol-4-yl]-4,7-difluoro-1H-imidazo[4,5-c]pyridine (2-2) (160 mg, 0.55 mmol, 1 equiv) and 3-[(3aS,4R,6aR)-2,2-dimethyl-4,6a-dihydro-3aH-cyclopenta[d][1,3]dioxol-4-yl]-4,7-difluoro-3H-imidazo[4,5-c]pyridine (2-1) (160 mg, 0.55 mmol, 1 equiv). The resulting solution was heated in a high pressure vessel to 85° C. for 4 days. The mixture was then concentrated and purified via flash chromatography on a 40 g silica gel column (gradient elution 0 to 100% ethyl acetate in dichloromethane and then 100% methanol to elute 2-3) to yield 1-[(3aS,4R,6aR)-2,2-dimethyl-4,6a-dihydro-3aH-cyclopenta[d][1,3]dioxol-4-yl]-7-fluoro-1H-imidazo[4,5-c]pyridin-4-amine (2-3) as a light yellow solid in addition to 3-[(3aS,4R,6aR)-2,2-dimethyl-4,6a-dihydro-3aH-cyclopenta[d][1,3]dioxol-4-yl]-7-fluoro-3H-imidazo[4,5-c]pyridin-4-amine (2-4) and recovered starting material 2-2. $^1$H NMR (2-3) (500 MHz, CDCl$_3$): δ 7.76 (d, J=3.0 Hz, 1H); 7.63 (s, 1H); 6.36 (d, J=5.7 Hz, 1H); 6.03 (d, J=5.7 Hz, 1H); 5.68 (s, 1H); 5.42 (d, J=5.6 Hz, 1H); 5.03 (s, 2H); 4.68 (d, J=5.7 Hz, 1H); 1.50 (t, J=9.7 Hz, 3H); 1.42-1.33 (m, 3H). LRMS m/z (M+H) 291.0 found, 291.1 required. $^1$H NMR (2-4) (500 MHz, CDCl$_3$): δ 7.77 (d, J=2.3 Hz, 1H); 7.73 (s, 1H); 6.47-6.43 (m, 1H); 6.17-6.14 (m, 1H); 5.87 (s, 1H); 5.41 (d, J=6.0 Hz, 1H); 5.00 (s, 2H); 4.69 (d, J=6.1 Hz, 1H); 1.55 (s, 3H); 1.38 (s, 3H). LRMS m/z (M+H) 291.0 found, 291.1 required.

(1S, 2R, 5R)-5-(4-amino-7-fluoro-1H-imidazo[4,5-c]pyridin-1-yl)cyclopent-3-ene-1,2-diol (2-5)

Concentrated HCl (3 mL) was added to 1-[(3aS,4R,6aR)-2,2-dimethyl-4,6a-dihydro-3aH-cyclopenta[d][1,3]dioxol-4-yl]-7-fluoro-1H-imidazo[4,5-c]pyridin-4-amine (2-3) (158 mg, 0.54 mmol, 1 equiv) in methanol (10 mL). After disappearance of the starting material, as monitored by LC-MS analysis, the mixture was concentrated to afford (1S,2R,5R)-5-(4-amino-7-fluoro-1H-imidazo[4,5-c]pyridin-1-yl)cyclopent-3-ene-1,2-dial (2-5) as a yellow solid of the bis-HCl salt. $^1$H NMR (2-5) (500 MHz, DMSO): δ 8.57 (s, 2H); 8.52 (s, 1H); 8.03 (d, J=5.3 Hz, 1H); 6.23 (d, J=5.9 Hz, 1H); 6.09 (d, J=6.2 Hz, 1H); 5.53 (d, J=5.5 Hz, 1H); 4.51 (s, 1H); 4.13 (t, J=5.7 Hz, 1H). HRMS m/z (M+H) 251.0939 found, 251.0939 required. $^1$H NMR (2-6) (500 MHz, DMSO): δ 8.53 (s, 1H); 8.24 (s, 2H); 8.08 (d, J=4.5 Hz, 1H); 6.32 (d, J=5.9 Hz, 1H); 6.21 (d, J=6.2 Hz, 1H); 5.71 (s, 1H); 4.54 (d, J=5.7 Hz, 1H); 4.08 (m, 1H). HRMS m/z (M+H) 251.0938 found, 251.0939 required.

Additional compounds 2-7 and 2-8 were synthesized, using the synthetic scheme described above for Example 2, with appropriate modifications within the knowledge of one skilled in the art.

| 2-7 | 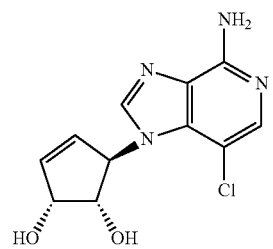 [SMILES: Nc1ncc(Cl)c2c1ncn2[C@@H]1C=C[C@@H](O)[C@H]1O] | (1S,2R,5R)-5-(4-amino-7-chloro-1H-imidazo[4,5-c]pyridin-1-yl)cyclopent-3-ene-1,2-diol | HRMS m/z (M + H) 267.0645 found, 267.0643 required. |
|---|---|---|---|
| 2-8 | 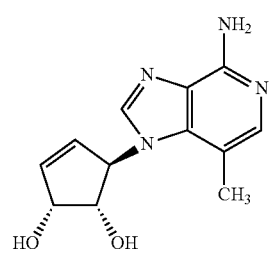 [SMILES: Cc1cnc(N)c2ncn([C@@H]3C=C[C@@H](O)[C@H]3O)c12] | (1S,2R,5R)-5-(4-amino-7-methyl-1H-imidazo[4,5-c]pyridin-1-yl)cyclopent-3-ene-1,2-diol | HRMS m/z (M + H) 247.1190 found, 247.1190 required. |

Example 3

(1S,2R,3S,4R)-4-(4-amino-7-fluoro-1H-imidazo[4,5-c]pyridin-1-yl)cyclopentane-1,2,3-triol

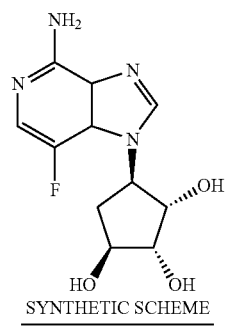

SYNTHETIC SCHEME

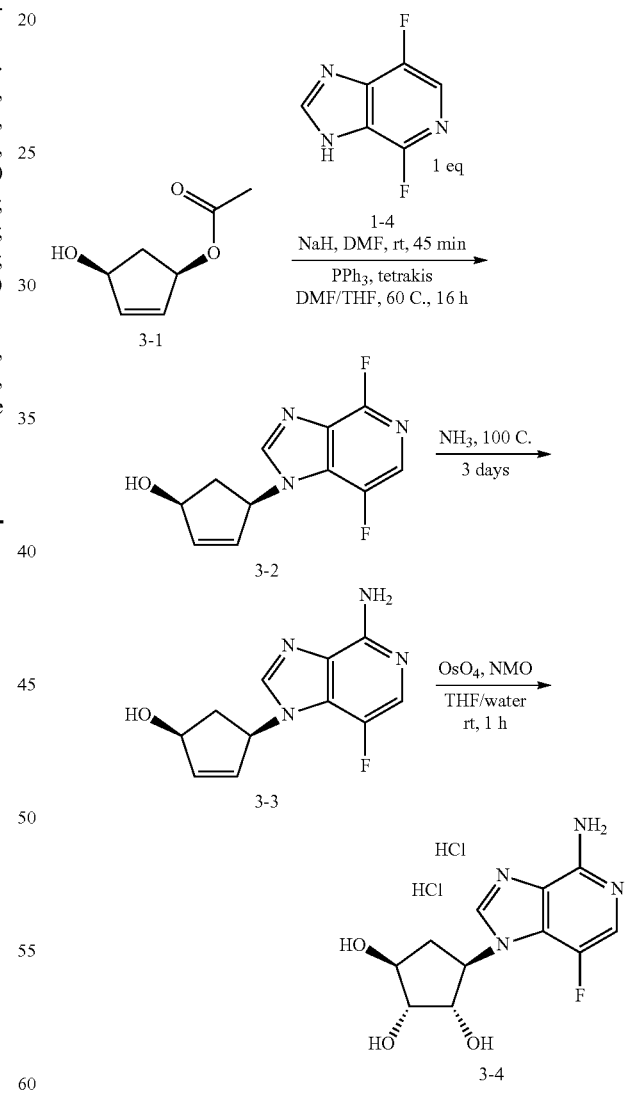

(1S,4R)-4-(4,7-difluoro-1H-imidazo[4,5-c]pyridin-1-yl)cyclopent-2-enol (3-2)

4,7-difluoro-1H-imidazo[4,5-c]pyridine (1-4) (2.0 g, 12.9 mmol, 1 equiv) was dissolved in dry DMF (21 mL). Sodium hydride (542 mg, 13.5 mmol, 1.05 equiv) was carefully added. The resulting mixture was stirred at ambient temperature for 45 minutes at which point triphenylphosphine (507 mg, 1.9 mmol, 0.15 equiv), Pd-tetrakis (745 mg, 0.6 mmol, 0.05 equiv) and (1R,3S)-(+)-cis-4-cyclopentene-1,3-diol 1-acetate (3-1) (2.2 g, 15.5 mmol, 1.2 equiv) in dry THF (21 mL) were added. The mixture was stirred at 60° C. for 16 hours, then cooled to ambient temperature, diluted with 100 mL EtOAc and washed with 50 mL water. The aqueous layer was washed with EtOAc three additional times, and the combined washings were dried over MgSO₄, filtered and concentrated. The crude residue was purified by reverse phase chromatography (5-95% CH₃CN/water with 0.1% TFA modifier) to afford (1S,4R)-4-(4,7-difluoro-1H-imidazo[4,5-c]pyridin-1-yl)cyclopent-2-enol (3-2) as a white solid. LRMS m/z (M+H) 238.0 found, 238.1 required.

(1S,4R)-4-(4-amino-7-fluoro-1H-imidazo[4,5-c]pyridin-1-yl)cyclopent-2-enol (3-3)

Liquid ammonia (100 mL) was added to (1S,4R)-4-(4,7-difluoro-1H-imidazo[4,5-c]pyridin-1-yl)cyclopent-2-enol (3-2) (220 mg, 0.6 mmol, 1 equiv). The resulting solution was heated in a high pressure vessel to 100° C. for 3 days. The mixture was then concentrated and purified via reverse phase chromatography (5-95% CH₃CN/water with 0.1% TFA modifier) to yield (1S,4R)-4-(4-amino-7-fluoro-1H-imidazo[4,5-c]pyridin-1-yl)cyclopent-2-enol (3-3) as a white solid. LRMS m/z (M+H) 235.0 found, 235.1 required.

(1S,2R,3S,4R)-4-(4-amino-7-fluoro-1H-imidazo[4,5-c]pyridin-1-yl)cyclopentane-1,2,3-triol (3-4)

(1S,4R)-4-(4-amino-7-fluoro-1H-imidazo[4,5-c]pyridin-1-yl)cyclopent-2-enol (3-3) (130 mg, 0.4 mmol, 1 equiv) was dissolved in THF (4.8 mL)/water (0.5 mL) and NMO (109 mg, 0.9 mmol, 2.5 equiv) and osmium tetroxide (0.9 mL, 0.08 mmol, 0.2 equiv, 2.5 wt. % in t-BuOH) was added. The resulting mixture was stirred at ambient temperature for 1 hour. Upon disappearance of starting material, the mixture was concentrated and purified by reverse phase chromatography (0-50% CH₃CN/water with 0.1% TFA modifier). The resulting product was dissolved in a solution of HCl in MeOH and concentrated to afford (1S,2R,3S,4R)-4-(4-amino-7-fluoro-1H-imidazo[4,5-c]pyridin-1-yl)cyclopentane-1,2,3-triol (3-4) as a white solid of the bis-HCl salt. ¹H NMR (500 MHz, CD3OD): δ 8.56 (s, 1H); 7.76 (d, J=5.0 Hz, 1H); 5.04 (q, J=7.5 Hz, 1H), 4.55 (dd, J=11.5, 4.5 Hz, 1H), 4.13 (dt, J=3.0, 6.5 Hz, 1H), 3.97 (d, J=4.5 Hz, 1H), 2.94 (m, 1H), 1.90 (m, 1H). LRMS m/z (M+H) 269.0 found, 269.1 required.

Example 4

(1S,2S,3R,5S)-3-(4-amino-7-fluoro-1H-imidazo[4,5-c]pyridin-1-yl)-5-fluorocyclopentane-1,2-diol

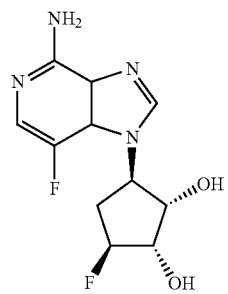

-continued
SYNTHETIC SCHEME

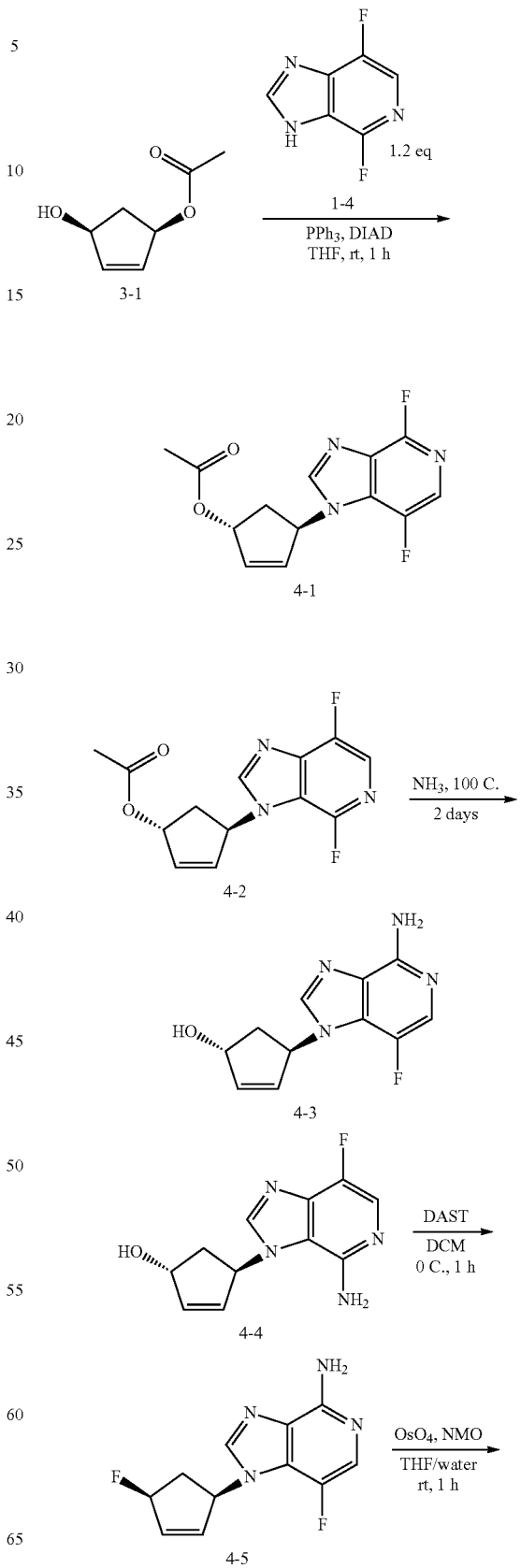

-continued

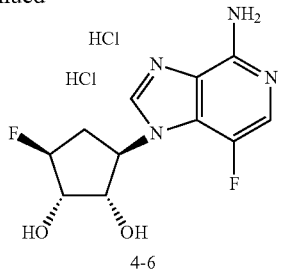

4-6

(1R,4R)-4-(4,7-difluoro-1H-imidazo[4,5-c]pyridin-1-yl)cyclopent-2-enyl acetate (4-1)

(1R,3S)-(+)-cis-4-cyclopentene-1,3-diol 1-acetate (3-1) (500 mg, 3.5 mmol, 1.0 equiv) was dissolved in dry THF (17.6 mL). Triphenylphosphine (1.4 g, 5.3 mmol, 1.5 equiv) was added, followed by 4,7-difluoro-1H-imidazo[4,5-c]pyridine (1-4) (655 mg, 4.2 mmol, 1.2 equiv). The mixture was cooled to 0° C. and DIAD (1 mL, 5.3 mmol, 1.5 equiv) was added dropwise. The resulting mixture was stirred at ambient temperature for 1 hour. Upon disappearance of starting material, the solvent was removed at reduced pressure and the yellow residue was purified via flash chromatography on a 120 g silica gel column (gradient elution 0 to 100% ethyl acetate in hexanes) to yield (1R,4R)-4-(4,7-difluoro-1H-imidazo[4,5-c]pyridin-1-yl)cyclopent-2-enyl acetate (4-1) and (1R,4R)-4-(4,7-difluoro-3H-imidazo[4,5-c]pyridin-3-yl)cyclopent-2-enyl acetate (4-2) as a 2:3 regioisomeric mixture. $^1$H NMR (4-1) (500 MHz, CDCl$_3$): δ 7.907 (s, 1H); 7.83 (t, J=2.5 Hz, 1H); 6.44 (m, 1H); 6.31 (m, 1H); 5.93-5.99 (m, 2H); 2.67 (m, 1H); 2.43 (m, 1H); 2.10 (s, 3H). LRMS m/z (M+H) 279.9 found, 280.1 required. $^1$H NMR (4-2) (500 MHz, CDCl$_3$): δ 7.98 (s, 1H); 7.81 (t, J=2 Hz, 1H); 6.44 (m, 1H); 6.31 (m, 1H); 5.93-5.99 (m, 2H); 2.67 (m, 1H); 2.43 (m, 1H); 2.10 (s, 3H). LRMS m/z (M+H) 279.9 found, 280.1 required.

(1R,4R)-4-(4-amino-7-fluoro-1H-imidazo[4,5-c]pyridin-1-yl)cyclopent-2-enol (4-3)

Liquid ammonia (150 mL) was added to a mixture of (1R,4R)-4-(4,7-difluoro-1H-imidazo[4,5-c]pyridin-1-yl)cyclopent-2-enyl acetate (4-1) (312 mg, 1.1 mmol, 1 equiv) and (1R,4R)-4-(4,7-difluoro-3H-imidazo[4,5-c]pyridin-3-yl)cyclopent-2-enyl acetate (4-2) (408 mg, 1.5 mmol, 1 equiv). The resulting solution was heated in a high pressure vessel to 100° C. for 2 days. The mixture was then concentrated and purified via reverse phase chromatography (5-95% CH$_3$CN/water with 0.1% TFA modifier) to yield (1R,4R)-4-(4-amino-7-fluoro-1H-imidazo[4,5-c]pyridin-1-yl)cyclopent-2-enol (4-3) as a white solid and (1R,4R)-4-(4-amino-7-fluoro-3H-imidazo[4,5-c]pyridin-3-yl)cyclopent-2-enol (4-4) as a white solid. $^1$H NMR (4-3) (500 MHz, CD$_3$OD): δ 8.03 (s, 1H); 7.61 (d, J=3.5 Hz, 1H); 6.31 (m, 1H); 6.20 (m, 1H); 5.93 (m, 1H); 5.09 (m, 1H); 2.40-2.50 (m, 1H); 2.27-2.37 (m, 1H). LRMS m/z (M+H) 235.0 found, 235.1 required. $^1$H NMR (4-4) (500 MHz, CD$_3$OD): δ 8.12 (s, 1H); 7.64 (d, J=2.5 Hz, 1H); 6.37 (m, 1H); 6.27 (m, 1H); 6.11 (m, 1H); 4.92 (m, 1H); 2.40-2.50 (m, 1H); 2.27-2.37 (m, 1H). LRMS m/z (M+H) 235.0 found, 235.1 required.

7-fluoro-1-((1R,4S)-4-fluorocyclopent-2-enyl)-1H-imidazo[4,5-c]pyridin-4-amine (4-5)

(1R,4R)-4-(4-amino-7-fluoro-1H-imidazo[4,5-c]pyridin-1-yl)cyclopent-2-enol (4-3) (600 mg, 2.6 mmol, 1 eq) was dissolved in DCM (120 mL). The mixture was cooled to 0° C. and DAST (1.6 mL, 12.0 mmol, 4.7 eq) was added. The resulting mixture was stirred at the same temperature for 1 hour. Upon disappearance of starting material, the reaction mixture was poured over NaHCO$_3$ (30 mL) and extracted with CHCl$_3$ (3×50 mL). The combined organics were dried over MgSO$_4$, filtered and concentrated. The crude residue was purified by flash chromatography (0-100% Acetone in DCM) to afford 7-fluoro-1-((1R,4S)-4-fluorocyclopent-2-enyl)-1H-imidazo[4,5-c]pyridin-4-amine (4-5) as a white solid. LRMS m/z (M+H) 236.9.0 found, 237.1 required.

(1S,2S,3R,5S)-3-(4-amino-7-fluoro-1H-imidazo[4,5-c]pyridin-1-yl)-5-fluorocyclopentane-1,2-diol (4-6)

7-fluoro-1-((1R,4S)-4-fluorocyclopent-2-enyl)-1H-imidazo[4,5-c]pyridin-4-amine (4-5) (180 mg, 0.8 mmol, 1 equiv) was dissolved in THF (9.8 mL)/water (1.1 mL) and NMO (223 mg, 1.9 mmol, 2.5 equiv) and osmium tetroxide (1.9 mL, 0.15 mmol, 0.2 equiv, 2.5 wt. % in t-BuOH) were added. The resulting mixture was stirred at ambient temperature for 1 hour. Upon disappearance of starting material, the mixture was concentrated and purified by reverse phase chromatography (0-50% CH$_3$CN/water with 0.1% TFA modifier). The resulting product was dissolved in a solution of HCl in MeOH and concentrated to afford (1S,2S,3R,5S)-3-(4-amino-7-fluoro-1H-imidazo[4,5-c]pyridin-1-yl)-5-fluorocyclopentane-1,2-diol (4-6) as a white solid of the bis-HCl salt. $^1$H NMR (500 MHz, CD3OD): δ 8.49 (s, 1H); 7.79 (d, J=5.5 Hz, 1H); 5.08 (q, J=9.0 Hz, 1H), 4.99 (m, 1H), 4.56 (m, 1H), 4.17 (dd, J=10, 4.5 Hz, 1H), 2.99-3.06 (m, 1H), 2.18-2.29 (m, 1H). LRMS m/z (M+H) 270.9 found, 271.1 required.

Example 5

(1R,2S,3S)-3-(4-amino-7-fluoro-1H-imidazo[4,5-c]pyridin-1-yl)-4-fluorocyclopentane-1,2-diol

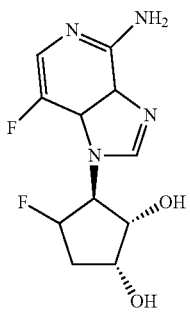

-continued
SYNTHETIC SCHEME
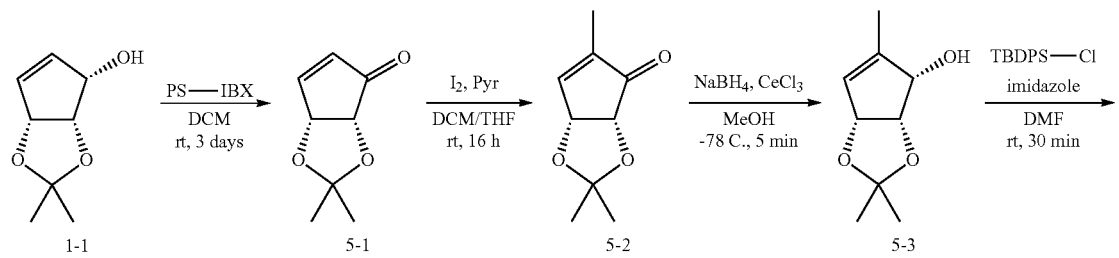
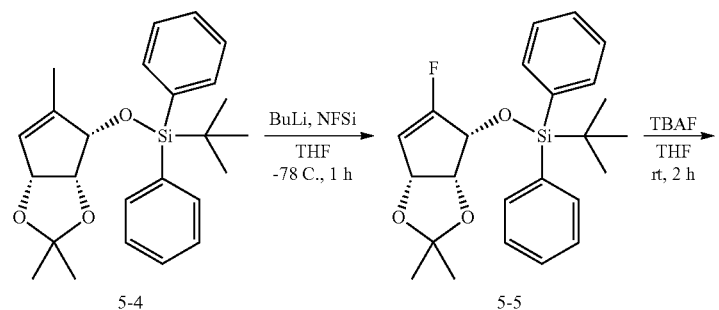
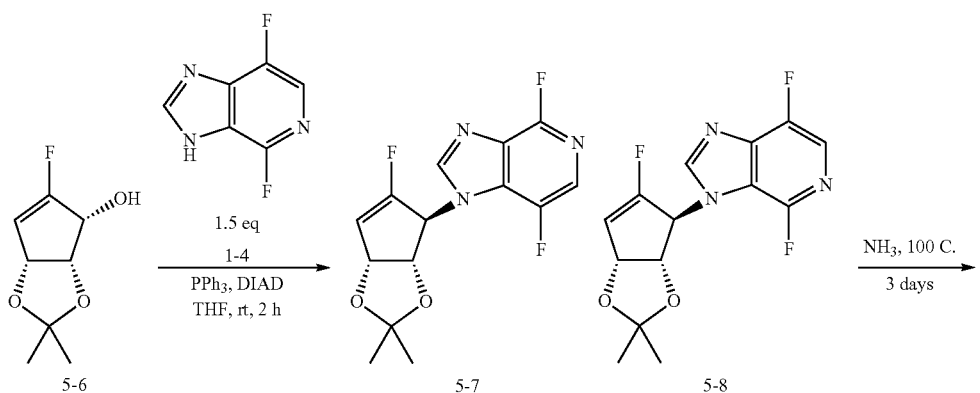
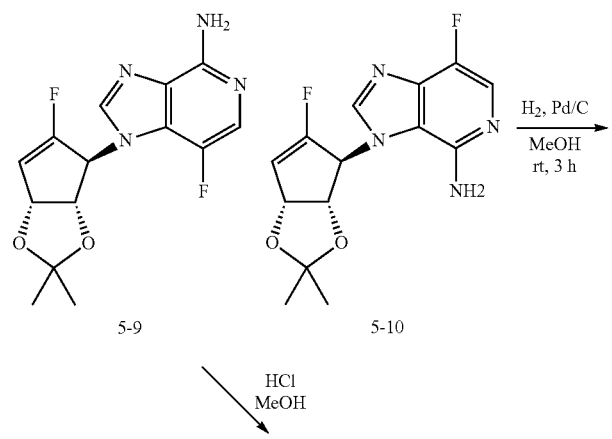

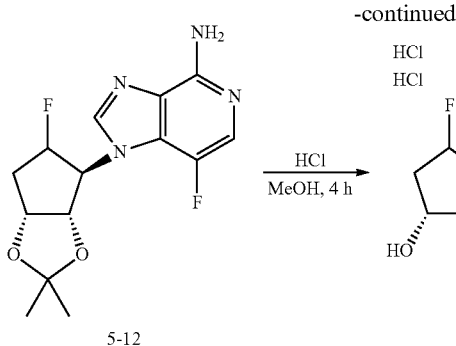

(3aR,6aR)-2,2-dimethyl-3aH-cycloenta[d][1,3]dioxol-4(6aH)-one 5-1)

(3aS,4S,6aR)-2,2-dimethyl-4,6a-dihydro-3aH-cyclopenta[d][1,3]dioxol-4-ol (1-1) (3 g, 19.2 mmol, 1 equiv) was dissolved in DCM (96 mL) and PS-IBX (32 g, 1.2 mmol/g loading, 2 equiv) was added. The mixture was rotated for 3 days at ambient temperature. Upon disappearance of starting material, the resin was filtered off washing with DCM (3×50 mL). The filtrate was concentrated to afford 3aR,6aR)-2,2-dimethyl-3aH-cyclopenta[d][1,3]dioxol-4(6aH)-one (5-1) as a tan solid. $^1$H NMR (500 MHz, CDCl$_3$): δ 7.61 (dd, J=5.5, 2.5 Hz, 1H); 6.21 (d, J=6.0 Hz, 1H); 5.27 (dd, J=5.5, 2.5 Hz, 1H); 4.46 (d, J=5.5 Hz, 1H); 1.41 (d, J=3.0 Hz, 6H).

(3aR,6aR)-5-iodo-2,2-dimethyl-3aH-cyclopenta[d][1,3]dioxol-4(6aH)-one (5-2)

3aR,6aR)-2,2-dimethyl-3aH-cyclopenta[d][1,3]dioxol-4(6aH)-one (5-1) (1.2 g, 7.8 mmol, 1 equiv) was dissolved in DCM (50 mL) and pyridine (0.9 mL, 10.9 mmol, 1.4 equiv) was added followed by a solution of iodine (3.4 g, 13.2 mmol, 1.7 equiv) in THF (6 mL). The resulting mixture stirred overnight at ambient temperature. Upon disappearance of starting material, the reaction mixture was poured over water (30 mL), extracted with CHCl$_3$ (3×50 mL), dried over MgSO$_4$, filtered and concentrated. The crude residue was purified by flash chromatography (80 g SiO$_2$, 0-40% EtOAc in hexanes) to yield (3aR,6aR)-5-iodo-2,2-dimethyl-3aH-cyclopenta[d][1,3]dioxol-4(6aH)-one (5-2) as a pale yellow solid. $^1$H NMR (500 MHz, CDCl$_3$): δ 7.97 (d, J=2.5 Hz, 1H); 5.22 (dd, J=5.5, 2.5 Hz, 1H); 4.53 (d, J=5.5 Hz, 1H); 1.42 (s, 3H); 1.39 (s, 3H).

(3aS,4R,6aR)-5-iodo-2,2-dimethyl-4,6a-dihydro-3aH-cyclopenta[d][1,3]dioxol-4-ol (5-3)

(3aR,6aR)-5-iodo-2,2-dimethyl-3aH-cyclopenta[d][1,3]dioxol-4(6aH)-one (5-2) (1.5 g, 5.4 mmol, 1 equiv) was dissolved in MeOH (54 mL). The solution was cooled to −78° C. and cerium(III) chloride (1.4 g, 5.7 mmol, 1.05 equiv) was added followed by sodium borohydride (216 mg, 5.7 mmol, 1.05 equiv). The resulting mixture was stirred at the same temperature for 5 minutes. Upon disappearance of the starting material, the reaction was quenched with the addition of water (10 mL) and concentrated. The residue was partitioned between EtOAc (100 mL) and water (40 mL), the organics were dried over MgSO$_4$, filtered and concentrated to afford (3aS,4R,6aR)-5-iodo-2,2-dimethyl-4,6a-dihydro-3aH-cyclopenta[d][1,3]dioxol-4-ol (5-3) as a pale yellow solid. $^1$H NMR (500 MHz, CDCl$_3$): δ 6.31 (s, 1H); 4.92 (dd, J=5.5, 2.0 Hz, 1H); 4.69 (t, J=5.5 Hz, 1H); 4.41 (dd, J=10.5, 5.5 Hz, 1H); 1.43 (s, 3H); 1.40 (s, 3H).

Tert-butyl((3aR,4R,6aR)-5-iodo-2,2-dimethyl-4,6a-dihydro-3aH-cyclopenta[d][1,3]dioxol-4-yloxy)diphenylsilane (5-4)

3aS,4R,6aR)-5-iodo-2,2-dimethyl-4,6a-dihydro-3aH-cyclopenta[d][1,3]dioxol-4-ol (5-3) (1.5 g, 5.3 mmol, 1 equiv) was dissolved in DMF (6 mL) and imidazole (1.3 g, 18/4 mmol, 3.5 equiv) was added followed by TBDPS-Cl (3.0 mL, 11.6 mmol, 2.2 equiv). The resulting mixture was stirred at ambient temperature for 30 minutes. Upon disappearance of starting material, the mixture was diluted with 50 mL EtOAc and washed with water (2×50 mL). The organic layer was dried over MgSO$_4$, filtered and concentrated. The crude residue was purified by flash chromatography (120 g SiO$_2$, 0-20% EtOAc in hexanes) to yield tert-butyl((3aR,4R,6aR)-5-iodo-2,2-dimethyl-4,6a-dihydro-3aH-cyclopenta[d][1,3]dioxol-4-yloxy)diphenylsilane (5-4) as a colorless oil. $^1$H NMR (500 MHz, CDCl$_3$): δ 7.82 (t, J=8 Hz, 4H); 7.34-7.44 (m, 6H); 6.33 (s, 1H); 4.61 (dd, J=5.5, 2.0 Hz, 1H); 4.46 (dd, J=5.5, 2.0 Hz, 1H); 3.91 (t, J=5.5 Hz, 1H); 1.40 (s, 3H); 1.21 (s, 3 II); 1.16 (s, 9H).

Tert-butyl((3aR,4R,6aR)-5-fluoro-2,2-dimethyl-4,6a-dihydro-3aH-cyclopenta[d][1,3]dioxol-4-yloxy)diphenylsilane (5-5)

Tert-butyl((3aR,4R,6aR)-5-iodo-2,2-dimethyl-4,6a-dihydro-3H-cyclopenta[d][1,3]dioxol-4-yloxy)diphenylsilane (5-4) (1.4 g, 2.7 mmol, 1 equiv) was dissolved in dry THF (18 mL) and N-fluorobenzenesulfonimide (1.0 g, 3.2 mmol, 1.2 equiv) was added. The resulting mixture was cooled to −78° C. and BuLi (3.2 mL, 8.0 mmol, 3 equiv, 2.5 M in hexanes) was added dropwise over 10 minutes. The mixture was stirred at the same temperature for 1 hour. Upon disappearance of the starting material, the reaction was quenched with the addition of 20 mL NH$_4$Cl, extracted with EtOAc (3×20 mL), dried over MgSO$_4$, filtered and concentrated. The crude residue was purified by flash chromatography (80 g SiO$_2$, 0-50% EtOAc in hexanes) to yield tert-butyl((3aR,4R,6aR)-5-fluoro-2,2-dimethyl-4,6a-dihydro-3aH-cyclopenta[d][1,3]dioxol-4-yloxy)diphenylsilane (5-5) as a colorless oil. $^1$H NMR (500 MHz, CDCl$_3$): δ 7.82 (d, J=5 Hz, 2H); 7.75 (d, J=6.5 Hz, 2H); 7.35-7.44 (m, 6H); 5.27 (s, 1H); 4.77 (dd, J=6.0, 2.0 Hz, 1H); 4.39 (t, J=6.0 Hz, 1H); 4.46 (td, J=6.0, 2.0 Hz, 1H); 1.52 (s, 3H); 1.35 (s, 3H); 1.10 (s, 9H).

(3aS,4R,6aR)-5-fluoro-2,2-dimethyl-4,6a-dihydro-3aH-cyclopenta[d][1,3]dioxol-4-ol (5-6)

Tert-butyl((3aR,4R,6aR)-5-fluoro-2,2-dimethyl-4,6a-dihydro-3aH-cyclopenta[d][1,3]dioxol-4-yloxy)diphenylsilane (5-5) (840 mg, 2.0 mmol, 1 eq) was dissolved in THF (10 mL) and TBAF (4.0 mL, 4.0 mmol, 2 equiv, 1M in THF) was added. The resulting mixture was stirred at ambient temperature for 2 hours. Upon disappearance of the starting material, the mixture was diluted with 50 mL EtOAc and washed with water (3×20 mL) and brine (20 mL). The organic layer was dried over MgSO$_4$, filtered and concentrated. The crude residue was purified by flash chromatography (40 g SiO$_2$, 0-60% EtOAc in hexanes) to yield (3aS,4R,6aR)-5-fluoro-2,2-dimethyl-4,6a-dihydro-3aH-cyclopenta[d][1,3]dioxol-4-ol (5-6) as a colorless oil. $^1$H NMR (500 MHz, CDCl$_3$): δ 5.31 (s, 1H); 4.98 (td, J=6.0, 2.0 Hz, 1H); 4.74 (td, J=6.0, 3.0 Hz, 1H); 4.44 (s, 1H); 2.88 (brs, 1H); 1.49 (s, 3H); 1.41 (s, 3H).

4,7-difluoro-1-((3aS,4S,6aR)-5-fluoro-2,2-dimethyl-4,6a-dihydro-3aH-cyclopenta[d][1,3]dioxol-4-yl)-1H-imidazo[4,5-c]pyridine (5-7)

(3S,4R,6aR)-5-fluoro-2,2-dimethyl-4,6a-dihydro-3aH-cyclopenta[d][1,3]dioxol-4-ol (5-6) (290 mg, 1.6 mmol, 1 equiv) was dissolved in dry THF (15 mL). Triphenylphosphine (620 mg, 2.4 mmol, 1.5 equiv) was added followed by 4,7-difluoro-1H-imidazo[4,5-c]pyridine (1-4) (370 mg, 2.4 mmol, 1.5 equiv). The mixture was cooled to 0° C. and DIAD (0.46 mL, 2.4 mmol, 1.5 equiv) was added dropwise. The resulting mixture was stirred at ambient temperature for 2 hours. Upon disappearance of the starting material, the solvent was removed at reduced pressure and the yellow residue was purified by flash chromatography (40 g SiO$_2$, 15-100% EtOAc in hexanes) to yield 4,7-difluoro-1-(3aS,4S,6aR)-5-fluoro-2,2-dimethyl-4,6a-dihydro-3aH-cyclopenta[d][1,3]dioxol-4-yl)-1H-imidazo[4,5-c]pyridine (5-7) and 4,7-difluoro-3-((3aS,4S,6aR)-5-fluoro-2,2-dimethyl-4,6a-dihydro-3aH-cyclopenta[d][1,3]dioxol-4-yl)-3H-imidazo[4,5-c]pyridine (5-8) as a 1:1 regioisomeric mixture. $^1$H NMR (5-7) (500 MHz, CDCl$_3$): δ 7.91 (s, 1H); 7.86 (t, J=2.0 Hz, 1H); 5.80 (s, 1H); 5.66 (s, 1H); 5.38 (m, 1H); 4.75 (q, J=5 Hz, 1H); 1.56 (s, 3H); 1.37 (s, 3H). LRMS m/z (M+H) 311.9 found, 312.1 required. $^1$H NMR (5-8) (500 MHz, CDCl$_3$): δ 7.99 (s, 1H); 7.89 (t, J=2.0 Hz, 1H); 5.80 (s, 1H); 5.66 (s, 1H); 5.38 (m, 1H); 4.75 (q, J=5 Hz, 1H); 1.56 (s, 3H); 1.37 (s, 3H). LRMS m/z (M+H) 311.9 found, 312.1 required.

7-fluoro-1-((3aS,4S,6aR)-5-fluoro-2,2-dimethyl-4,6a-dihydro-3aH-cyclopenta[d][1,3]dioxol-4-yl)-1H-imidazo[4,5-c]pyridin-4-amine (5-9)

Liquid ammonia (150 mL) was added to a mixture of 4,7-difluoro-1-((3aS,4S,6aR)-5-fluoro-2,2-dimethyl-4,6a-dihydro-3aH-cyclopenta[d][1,3]dioxol-4-yl)-1H-imidazo[4,5-c]pyridine (5-7) (140 mg, 0.45 mmol, 1 equiv) and 4,7-difluoro-3-((3aS,4S,6aR)-5-fluoro-2,2-dimethyl-4,6a-dihydro-3aH-cyclopenta[d][1,3]dioxol-4-yl)-3H-imidazo[4,5-c]pyridine (5-8) (160 mg, 0.51 mmol, 1 equiv). The resulting solution was heated in a high pressure vessel to 100° C. for 3 days. The mixture was then concentrated and purified via flash chromatography (40 g SiO$_2$; 20-100% EtOAc in hexanes, holding at 100% EtOAc to elute 5-9) to yield 7-fluoro-1-((3aS,4S,6aR)-5-fluoro-2,2-dimethyl-4,6a-dihydro-3aH-cyclopenta[d][1,3]dioxol-4-yl)-1H-imidazo[4,5-c]pyridin-4-amine (5-9) as a white solid and 7-fluoro-3-((3aS,4R,6aR)-5-fluoro-2,2-dimethyl-4,6a-dihydro-3aH-cyclopenta[d][1,3]dioxol-4-yl)-3H-imidazo[4,5-c]pyridin-4-amine (5-10) as a white solid. $^1$H NMR (5-9) (500 MHz, CDCl$_3$): δ 7.77 (d, J=3.5 Hz, 1H); 7.71 (s, 1H); 5.74 (s, 1H); 5.58 (s, 1H); 5.36 (m, 1H); 5.12 (s, 2H); 4.75 (t, J=5 Hz, 1H); 1.55 (s, 3H); 1.36 (s, 3H). LRMS m/z (M+H) 308.9 found, 309.1 required. LRMS m/z (5-10) (M+H) 308.9 found, 309.1 required.

(1S,2R,5S)-5-(4-amino-7-fluoro-1H-imidazo[4,5-c]pyridin-3-yl)-4-fluorocyclopent-3-ene-1,2-diol (5-11)

7-fluoro-1-((3 aS,4S,6aR)-5-fluoro-2,2-dimethyl-4,6a-dihydro-3aH-cyclopenta [d][1,3]dioxol-4-yl)-1H-imidazo[4,5-c]pyridin-4-amine (5-9) (3.6 mg, 0.012 mmol, 1 equiv) was dissolved in MeOH (0.5 mL) and concentrated HCl (50 uL) was added. After disappearance of the starting material, the mixture was concentrated to afford (1S,2R,5S)-5-(4-amino-7-fluoro-1H-imidazo[4,5-c]pyridin-3-yl)-4-fluorocyclopent-3-ene-1,2-diol (5-11) as a white solid of the bis-HCl salt. $^1$H NMR (500 MHz, CD$_3$OD): δ 8.46 (s, 1H); 7.81 (d, J=5.5 Hz, 1H); 5.78 (m, 1H); 5.73 (m, 1H); 4.69 (m, 1H); 4.42 (t, J=5.5 Hz, 1H). LRMS m/z (M+H) 269.0 found, 269.1 required.

7-fluoro-1-((3aS,4S,6aR)-5-fluoro-2,2-dimethyltetrahydro-3aH-cyclopenta [d][1,3]dioxol-4-yl)-1H-imidazo[4,5-c]pyridin-4-amine (5-12)

7-fluoro-1-((3aS,4S,6aR)-5-fluoro-2,2-dimethyl-4,6a-dihydro-3aH-cyclopenta [d][1,3]dioxol-4-yl)-1H-imidazo[4,5-c]pyridin-4-amine (5-9) (70 mg, 0.23 mmol, 1 equiv) was dissolved in MeOH (5 mL), the system was placed under nitrogen and 10% Pd/C (25 mg, 0.23 mmol, 1 equiv) was carefully added. The resulting mixture was stirred under a H$_2$ atmosphere (1 atm) until disappearance of the starting material. Hydrogen was removed followed by filtration through a celite plug and washing of the solids with MeOH (4×20 mL). The filtrate was concentrated and the residue was purified via reverse phase chromatography (0-50% CH$_3$CN in water with 0.1% TFA modifier) to afford 7-fluoro-1-((3aS,4S,6aR)-5-fluoro-2,2-dimethyltetrahydro-3aH-cyclopenta[d][1,3]dioxol-4-yl)-1H-imidazo[4,5-c]pyridin-4-amine (5-12) as a white solid. $^1$H NMR (500 MHz, CDCl$_3$): δ 7.78 (d, J=3.5 Hz, 1H); 7.73 (s, 1H); 5.20-5.38 (m, 1H); 5.07 (s, 1H); 4.92 (m, 1H); 4.82 (s, 1H); 2.72-2.78 (m, 1H); 2.26-2.37 (m, 1H); 1.61 (s, 3H); 1.32 (s, 3H). LRMS m/z (M+H) 311.0 found, 311.1 required.

(1R,2S,3S)-3-(4-amino-7-fluoro-1H-imidazo[4,5-c]pyridin-1-yl)-4-fluorocyclopentane-1,2-diol (5-13)

7-fluoro-1-((3aS,4S,6aR)-5-fluoro-2,2-dimethyltetrahydro-3aH-cyclopenta[d][1,3]dioxol-4-yl)-1H-imidazo[4,5-c]pyridin-4-amine (5-12) (30 mg, 0.1 mmol, 1 equiv) was dissolved in MeOH (1 mL) and concentrated HCl (200 uL) was added. After disappearance of the starting material, the mixture was concentrated to afford (1R,2S,3S)-3-(4-amino-7-fluoro-1H-imidazo[4,5-c]pyridin-1-yl)-4-fluorocyclopentane-1,2-diol (5-13) as a white solid of the bis-HCl salt. $^1$H NMR (500 MHz, CD$_3$OD): δ 8.59 (s, 1H); 7.82 (d, J=5.0 Hz, 1H); 5.31-5.38 (m, 1H); 5.28 (d, J=8.5 Hz, 1H); 4.35 (m, 1H);

4.19 (t, J=5.0 Hz, 1H); 2.63 (m, 1H); 2.05 (dd, J=27.5, 16.5 Hz, 1H). LRMS m/z (M+H) 270.9 found, 271.1 required.

Example 6

(1R,2S,3R,5S)-3-(4-amino-7-fluoro-3a,7a-dihydro-1H-imidazo[4,5-c]pyridin-1-yl)-5-methylcyclopentane-1,2-diol

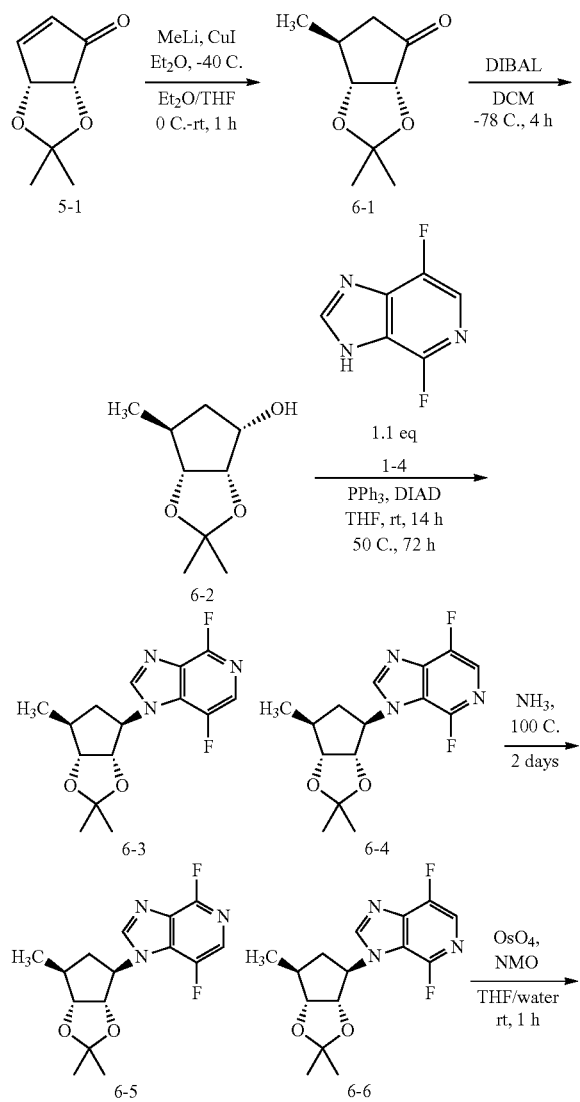

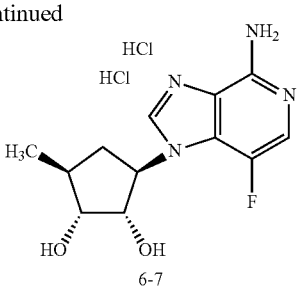

(3aR,6S,6aR)-2,2,6-trimethyldihydro-3aH-cyclopenta[d][1,3]dioxol-4(5H)-one (6-1)

Copper(I) iodide (3.7 g, 19.5 mmol, 5 equiv) was suspended in $Et_2O$ (35 mL) and cooled to −40° C. Methyllithium (20.2 mL, 32.3 mmol, 8.3 equiv, 1.6M in THF) was added dropwise over 45 minutes. The mixture was warmed to 0° C. and (3aR,6aR)-2,2-dimethyl-3aH-cyclopenta[d][1,3]dioxol-4(6aH)-one (5-1) (600 mg, 3.9 mmol, 1 equiv) in 1:1 THF/$Et_2O$ (20 mL) was added dropwise over 10 minutes. The resulting mixture was stirred warming to ambient temperature over 1 hour. The mixture was then cooled to 0° C., quenched carefully with 25 mL of 15% acetic acid and extracted with EtOAc (3×40 mL). The combined organics were washed with $NH_4Cl$ (50 mL), dilute $NH_4OH$ (2×50 mL) and water (50 mL), dried over $MgSO_4$, filtered and concentrated to afford (3aR,6S,6aR)-2,2,6-trimethyldihydro-3aH-cyclopenta[d][1,3]dioxol-4(5H)-one (6-1) as a light yellow oil. $^1H$ NMR (500 MHz, $CDCl_3$): δ 4.50 (d, J=5.5 Hz, 1H); 4.23 (d, J=5.0 Hz, 1H); 2.80 (dd, J=18.5, 8.0 Hz, 1H); 2.53 (quin, J=8.0 Hz, 1H); 1.96 (d, J=18.5 Hz, 1H); 1.43 (s, 3H); 1.35 (s, 3H); 1.05 (d, J=7.5 Hz, 3H).

(3aS,4S,6S,6aR)-2,2,6-trimethyltetrahydro-3aH-cyclopenta[d][1,3]dioxol-4-ol (6-2)

(3aR,6S,6aR)-2,2,6-trimethyldihydro-3aH-cyclopenta[d][1,3]dioxol-4(5H)-one (6-1) (490 mg, 2.7 mmol, 1 equiv) was dissolved in dry DCM (55 mL) and 3A molecular sieves were added. The mixture was cooled to −78° C. and DIBAL (4.1 mL, 4.1 mmol, 1.5 equiv, 1.0M in heptane) was added dropwise. The resulting mixture stirred at the same temperature for 4 hours. Upon disappearance of the starting material, MeOH (6 mL) was added to quench the reaction. Water (10 mL) was added and the mixture was filtered through celite washing with DCM (2×30 mL). The organic layer was separated, dried over $MgSO_4$, filtered and concentrated to afford (3aS,4S,6S,6aR)-2,2,6-trimethyltetrahydro-3aH-cyclopenta[d][1,3]dioxol-4-ol (6-2) as a colorless oil. $^1H$ NMR (500 MHz, $CDCl_3$): δ 4.50 (t, J=6.0 Hz, 1H); 4.27 (d, J=5.5 Hz, 1H); 4.12 (quin, J=6.0 Hz, 1H); 2.46 (d, J=8.5 Hz, 1H); 2.15 (quirt, J=4.5 Hz, 1H); 1.85 (m, 1H); 1.64 (dq, J=12.5, 3.0 Hz, 1H); 1.49 (s, 3H); 1.34 (s, 3H); 0.93 (d, J=8.0 Hz, 3H).

4,7-difluoro-1-((3aS,4R,6S,6aR)-2,2,6-trimethyltetrahydro-3aH-cyclopenta[d][1,3]dioxol-4-yl)-1H-imidazo[4,5-c]pyridine (6-3)

(3aS,4S,6S,6aR)-2,2,6-trimethyltetrahydro-3aH-cyclopenta[d][1,3]dioxol-4-ol (6-2) (400 mg, 2.3 mmol, 1 equiv) was dissolved in THF (25 mL). Triphenylphosphine (914 mg, 3.5 mmol, 1.5 equiv) was added followed by 4,7-difluoro-1H-imidazo[4,5-c]pyridine (1-4) (396 mg, 2.6 mmol, 1.1 equiv).

The mixture was cooled to 0° C. and DIAD (0.72 mL, 3.7 mmol, 1.6 equiv) was added dropwise. The resulting mixture was stirred at ambient temperature for 14 hours and then heated to 50° C. for an additional 72 hours. The solvent was removed at reduced pressure and the yellow residue was purified via flash chromatography (40 g SiO2, 15-100% EtOAc in hexanes) to yield 4,7-difluoro-1-((3aS,4R,6S,6aR)-2,2,6-trimethyltetrahydro-3aH-cyclopenta[d][1,3]dioxol-4-yl)-1H-imidazo[4,5-c]pyridine (6-3) and 4,7-difluoro-3-((3aS,4R,6S,6aR)-2,2,6-trimethyltetrahydro-3aH-cyclopenta[d][1,3]dioxol-4-yl)-3H-imidazo[4,5-c]pyridine (6-4) as a 1:1 regioisomeric mixture. $^1$H NMR (6-3) (500 MHz, CDCl$_3$): δ 8.02 (s, 1H); 7.84 (t, J=4.5 Hz, 1H); 4.80-4.91 (m, 2H); 4.41 (q, J=6.5 Hz, 1H); 2.53 (sextuplet, J=6.5 Hz, 1H); 2.29 (septuplet, J=6.0 Hz, 1H); 2.00 (m, 1H); 1.57 (s, 3H); 1.31 (s, 3H); 1.25 (d, J=6.5 Hz, 3H). LRMS m/z (M+H) 309.9 found, 310.1 required. $^1$H NMR (6-4) (500 MHz, CDCl$_3$): δ 8.10 (s, 1H); 7.81 (t, J=5.0 Hz, 1H); 4.80-4.91 (m, 2H); 4.41 (q, J=6.5 Hz, 1H); 2.53 (sextuplet, J=6.5 Hz, 1H); 2.29 (septuplet, J=6.0 Hz, 1H); 2.00 (m, 1H); 1.57 (s, 3H); 1.31 (s, 3H); 1.25 (d, J=6.5 Hz, 3H). LRMS m/z (M+H) 309.9 found, 310.1 required.

7-fluoro-1-((3aS,4R,6S,6aR)-2,2,6-trimethyltetrahydro-3aH-cyclopenta[d][1,3]dioxol-4-yl)-1H-imidazo[4,5-c]pyridin-4-amine (6-5)

Liquid ammonia (150 mL) was added to a mixture of 4,7-difluoro-1-((3aS,4R,6S,6aR)-2,2,6-trimethyltetrahydro-3aH-cyclopenta[d][1,3]dioxol-4-yl)-1H-imidazo[4,5-c]pyridine (6-3) (180 mg, 0.6 mmol, 1 equiv) and 4,7-difluoro-3-((3aS,4R,6S,6aR)-2,2,6-trimethyltetrahydro-3aH-cyclopenta[d][1,3]dioxol-4-yl)-3H-imidazo[4,5-c]pyridine (6-4) (180 mg, 0.6 mmol, 1 equiv). The resulting solution was heated in a high pressure vessel to 100° C. for 2 days. The mixture was then concentrated and purified by flash chromatography (12 g SiO$_2$; 20-100% EtOAc in hexanes and then 100% ethanol to elute 6-3) to yield 7-fluoro-1-((3aS,4R,6S,6aR)-2,2,6-trimethyltetrahydro-3aH-cyclopenta[d][1,3]dioxol-4-yl)-1H-imidazo[4,5-c]pyridin-4-amine (6-5) as a tan solid and 7-fluoro-3-((3aS,4R,6S,6aR)-2,2,6-trimethyltetrahydro-3aH-cyclopenta[d][1,3]dioxol-4-yl)-3H-imidazo[4,5-c]pyridin-4-amine (6-6) as a tan solid. LRMS m/z (M+H) 306.9 found, 307.1 required.

(1R,2S,3R,5S)-3-(4-amino-7-fluoro-3a,7a-dihydro-1H-imidazo[4,5-c]pyridin-1-yl)-5-methylcyclopentane-1,2-diol (6-7)

7-fluoro-1-((3aS,4R,6S,6aR)-2,2,6-trimethyltetrahydro-3aH-cyclopenta[d][1,3]dioxol-4-yl)-1H-imidazo[4,5-c]pyridin-4-amine (6-5) was dissolved in MeOH (1 mL) and concentrated HCl (200 uL) was added. After disappearance of the starting material, the mixture was concentrated to afford (1R,2S,3R,5S)-3-(4-amino-7-fluoro-3a,7a-dihydro-1H-imidazo[4,5-c]pyridin-1-yl)-5-methylcyclopentane-1,2-diol (6-7) as a brown solid. $^1$H NMR (500 MHz, CD$_3$OD): δ 8.54 (s, 1H); 7.77 (d, J=5.6 Hz, 1H); 4.95 (q, J=8.5 Hz, 1H); 4.33 (t, J=6.5 Hz, 1H); 3.76 (t, J=6.0 Hz, 1H); 2.54 (m, 1H); 2.11 (m, 1H); 1.60 (q, J=11.0 Hz, 1H); 1.21 (d, J=7.5 Hz, 3H). LRMS m/z (M+H) 267.0 found, 267.1 required.

In vitro AHCY Activity Assay

The AHCY activity of the compounds of the invention can be measured by the following in vitro assay.

The AHCY enzyme assay is based on the principle of fluorescence emission following incubation of a reactive dye with the products of an AHCY catalyzed reaction. The reactive dye (Thioglo1) binds homocysteine through its thiol-containing moiety. The products of the AHCY catalyzed reaction, adenosine and homocysteine, are produced from the hydrolysis of SAH (s-adenosylhomocysteine) through AHCY's hydrolase activity.

The reaction is optimized in 96-, 384-, 1536- and 3456-assay plate formats, with recombinant expressed human or mouse AHCY enzyme. When run under initial velocity conditions, the assay is suitable for IC50 and % inhibition calculations.

Materials:
1) ThioGlo1 (catalog 595501, Calbiochem); 100 mM in DMSO
2) SAH (catalog A-9384, Sigma); 4.69 mM with 0.06 N HCl
3) Aristeromycin (catalog A-0928, Sigma); 100 mM in DMSO
4) NAD (catalog 43410, Sigma); 14.5 mM in water
5) EDTA in 500 mM pH 8 (catalog BP2482-100, Fisher)
6) DTT stock 200 mM in water
7) AHCY enzyme (diluted with 100 mM tris pH7.5)

Dilutions Immediately Prior to use:
1. SAH 750 μM (10×) (dilute with 100 mM Tris pH 7.5)
2. Aristeromycin (10×) (dilute to 1 mM with 100 mM Tris pH7.5)
3. ThioGlo1 (10×) (dilute to 100 μM in Tris pH7.5)
4. AHCY assay buffer (3.3×): 3 μM DTT, 150 μM NAD, 3 mM EDTA Protocol: As per 96-Assay Plate Well
1. Add 5 μL AHCY enzyme [30 ng/ul in 100 mM Tris pH7.5]
2. Add 5 μL DMSO or inhibitor
3. Add 15 μL AHCY assay buffer
4. Add 15 μL 100 mM Tris pH 7.5
5. Incubate 37° C. 30 min
6. Add 5 μL 750 uM SAH
7. Incubate 37° C. 10 min
8. Add 5 μl 100 μM ThioGlo1
9. Incubate 37° C. 15 mins
10. Read plate (Ex 380 Em 510)

Example 1 was tested according to this protocol (n=3) and gave an average IC$_{50}$=42 nM. Example 2 was tested according to this protocol (n=1) and gave an IC$_{50}$=17,900 nM. These values attest to the properties of these compounds as potent inhibitors of the enzyme AHCY.

Cell-Based Assay of AHCY Inhibition

The AHCY activity of the compounds of the invention can be measured by the following cell-based assay.

This assay measures secreted homocysteine over a period of time from adherent HEK293 and/or SH-SY5Y cells as a measure of the ability of a compound to enter a cell in culture and effectively inhibit AHCY in the context of the cellular milieu. Post treatment collection of the adherent Hek293 and/or SH-SY5Y cells is also made for a viability and proliferation measure. Since the amount of secreted homocysteine is limited by the amount of SAH that is converted to homocysteine in the cells and its subsequent secretion, an EC50 measure and % inhibition relative to DMSO control cells can be made. Since the amount of secreted metabolites such as homocysteine can also be related to the absolute and cellular viability, an MTT (3-(4,5-Dimethylthiazol-2-yl)-2,5-diphenyltetrazolium bromide) measure of proliferation and relative cytotoxicty (as compared to control conditions) may also be made.

Protocol:
1. The day before compound treatment, plate 20,000 cells (Hek293 or SH-SY5Y) in 96 well cell culture treated plates in 100 µl of cell culture media (DMEM and 10% fetal bovine serum).
2. Add fresh media plus compound (and DMSO treated controls) for 72 hrs.
3. Collect conditioned media for measurement of secreted homocysteine and perform viability/proliferation assay on adherent cells.

Measure of Secreted Homocysteine:
1. Add 25 µl conditioned media, standard or control in 96-well assay plate
2. Add 25 µl internal standard
3. Add 10 µl reduction solution
4. Add 50 µl derivatisation reagent
5. Incubate for 10 min in PCR (polymerase chain reaction) machine at 60° C., stop reaction at 4° C. or on ice.
6. Add 50 µl precipitating solution
7. Mix well, incubate for 10 min at 4° C. and centrifuge for 10 min at 2,000×
8. Inject 20 µl of the supernatant into HPLC system.
    a. Chromatographic conditions:
        i. Column material: Imtakt Unisom C18, 3 µm
        ii. Column dimension: 50 mm×4.6 mm
        iii. Flow rate: 1.5 ml/min
        iv. Detection: Fluorescence: Excitation 385 DM, Emission 515 nm
        v. Injection volume: 20 µl
        vi. Running time: 3.5 min
    b. Calculation:
    c. (peak height patient*concentration of the calibrator/peak height internal standard patient) *F=concentration patient sample (F=1S peak of calibrator/Hcy peak of calibrator)

Measure of Cell Viability/Proliferation:
1. Add mixture of 10 µl 5 mg/ml MTT labeling reagent plus 90 µl fresh assay media to cells.
2. Incubate for 4 hrs at 37° C. in cell culture incubator
3. Add 100 µl of solubilization solution.
4. Incubate for 16 hrs at 37° C. in cell culture incubator
5. ReaDMEMd absorbance at 550 nM and 690 nM.
6. Express readout as 550 nM-690 nM.

Example 1 was tested according to this protocol (n=4) and gave an average $IC_{50}$=1.5 nM. Example 2 was tested according to this protocol (n=1) and gave an $IC_{50}$=28.2 nM. These values attest to the properties of these compounds as potent inhibitors of AHCY in a cell-based format and their ability to lower homocysteine concentration intracellularly.

The following abbreviations are used throughout the text:
AdoHcy S-Adenosyl homocysteine
Me: methyl
Et: ethyl
t-Bu: tent-butyl
i-Pr: isopropyl
Ph: phenyl
DCM: dichloromethane
THF: tetrahydrofuran
Ac: acetyl
NAD: nicotinamide adenine dinucleotide
DMEM: Dulbecco's modified Eagle's medium
MTT: 3-(4,5-Dimethylthiazol-2-yl)-2,5-diphenyltetrazolium bromide
PCR: polymerase chain reaction
DMSO: dimethylsulfoxide
rt: room temperature
aq: aqueous
HPLC: high performance liquid chromatography
MS: mass spectrometry
$CDCl_3$: chloroform-d
DMF: N,N-dimethylformamide
LRMS: low resolution mass spectrum
NMR: nuclear magnetic resonance While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

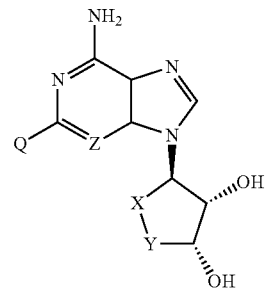

or a pharmaceutically acceptable salt thereof, wherein
X—Y is selected from the group consisting of
  (1) $CR^1R^2$—$CR^3R^4$,
  (2) $CR^1$=$CR^2$;
Z is —$CR^5$;
Q is selected from the group consisting of
  (1) hydrogen,
  (2) halogen, and
  (2) —$C_{1-6}$ alkyl;
$R^1$, $R^2$, $R^3$ and $R^4$ are each independently selected from the group consisting of
  (1) hydrogen,
  (2) hydroxyl,
  (3) halogen,
  (4) —$C_{1-6}$ alkyl, wherein said alkyl is optionally substituted with
    (a) halogen, or
    (b) hydroxyl;
$R^5$ is selected from the group consisting of
  (1) hydrogen,
  (2) —$C_{1-6}$ alkyl, and
  (3) —$C_{3-6}$ cycloalkyl.

2. The compound of claim 1, or a pharmaceutically acceptable salt thereof, wherein Z is —$CR^5$—, wherein $R^5$ is halogen.

3. The compound of claim 1, or a pharmaceutically acceptable salt thereof, wherein X—Y is $CR^1R^2$—$CR^3R^4$.

4. The compound of claim 3, or a pharmaceutically acceptable salt thereof, wherein each of $R^1$, $R^2$, $R^3$ and $R^4$ is selected from the group consisting of
  (1) hydrogen, and
  (2) —$C_{1-3}$ alkyl, wherein said alkyl is optionally substituted with
    (a) halogen, or
    (b) hydroxyl.

5. The compound of claim 4, or a pharmaceutically acceptable salt thereof, wherein each of $R^1$, $R^2$, $R^3$ and $R^4$ is selected from the group consisting of
(1) hydrogen, and
(2) —CH$_2$OH.

6. The compound of claim 5, or a pharmaceutically acceptable salt thereof, wherein each of $R^1$, $R^2$, $R^3$ and $R^4$ is hydrogen.

7. The compound of claim 1, or a pharmaceutically acceptable salt thereof, wherein X—Y is $CR^1$=$CR^2$.

8. The compound of claim 7, or a pharmaceutically acceptable salt thereof, wherein each of $R^1$ and $R^2$ is selected from the group consisting of
(1) hydrogen, and
(2) —C$_{1-3}$ alkyl, wherein said alkyl is optionally substituted with
    (a) halogen, or
    (b) hydroxyl.

9. The compound of claim 8, or a pharmaceutically acceptable salt thereof, wherein each of $R^1$ and $R^2$ is selected from the group consisting of
(1) hydrogen, and
(2) —CH$_2$OH.

10. The compound of claim 7, or a pharmaceutically acceptable salt thereof, wherein X—Y is CH=$CR^2$, wherein $R^2$ is selected from the group consisting of
(1) hydrogen, and
(2) —C$_{1-3}$ alkyl, wherein said alkyl is optionally substituted with
    (a) halogen, or
    (b) hydroxyl.

11. The compound of claim 7, or a pharmaceutically acceptable salt thereof, wherein X—Y is —CH=CH—.

12. The compound of claim 1, wherein $R^5$ is selected from the group consisting of
(1) halogen, and
(2) —C$_{1-3}$ alkyl, wherein said alkyl is optionally substituted with
    (a) halogen, or
    (b) hydroxyl.

13. The compound of claim 1, wherein Q is hydrogen or halogen.

14. The compound of claim 13, wherein Q is hydrogen.

15. The compound of claim 1, which is selected from the group consisting of
(1R,2S,3R)-3-(4-amino-7-fluoro-1H-imidazo[4,5-c]pyridin-1-yl)cyclopentane-1,2-diol (1); (1R,2S,3R)-3-(4-amino-7-chloro-1H-imidazo[4,5-c]pyridin-1-yl)cyclopentane-1,2-diol(1-11);
(1R,2S,3R)-3-(4-amino-7-methyl-1H-imidazo[4,5-c]pyridin-1-yl)cyclopentane-1,2-diol(1-12);
(1R,2S,3R)-3-(4-amino-6,7-difluoro-1H-imidazo[4,5-c]pyridin-1-yl)cyclopentane-1,2-diol(1-15);
(1R,2R,5R)-5-(4-amino-7-chloro-1H-imidazo[4,5-c]pyridin-1-yl)cyclopent-3-ene-1,2-diol(2-7);
(1R,2R,5R)-5-(4-amino-7-methyl-1H-imidazo[4,5-c]pyridin-1-yl)cyclopent-3-ene-1,2-diol (2-8);
(1R,2R,3S,4R)-4-(4-amino-7-fluoro-1H-imidazo[4,5-c]pyridin-1-yl)cyclopentane-1,2,3-triol(3);
(1R,2S,3R,5S)-3-(4-amino-7-fluoro-1H-imidazo[4,5-c]pyridin-1-yl)-5-fluorocyclopentane-1,2-diol(4);
(1R,2S,3S)-3-(4-amino-7-fluoro-1H-imidazo[4,5-c]pyridin-1-yl)-4-fluorocyclopentane-1,2-diol(5);
(1R,2S,3R,5S)-3-(4-amino-7-fluoro-3a,7a-dihydro-1H-imidazo[4,5-c]pyridin-1-yl)-5-methylcyclopentane-1,2-diol(6);
or a pharmaceutically acceptable salt thereof.

16. A pharmaceutical composition comprising a compound of claim 1 or a pharmaceutically acceptable salt thereof, and a pharmaceutically acceptable carrier.

* * * * *